(12) United States Patent
Reddy

(10) Patent No.: US 12,268,717 B1
(45) Date of Patent: Apr. 8, 2025

(54) ENHANCED MICROBIAL THERAPEUTIC AGENTS

(71) Applicant: Malireddy S. Reddy, Cherry Hills Village, CO (US)

(72) Inventor: Malireddy S. Reddy, Cherry Hills Village, CO (US)

( * ) Notice: Subject to any disclaimer, the term of this patent is extended or adjusted under 35 U.S.C. 154(b) by 0 days.

(21) Appl. No.: 18/593,739

(22) Filed: Mar. 1, 2024

(51) Int. Cl.
| | | |
|---|---|---|
| A61K 35/744 | (2015.01) | |
| A61K 35/00 | (2006.01) | |
| A61K 35/741 | (2015.01) | |
| A61K 35/742 | (2015.01) | |
| A61K 35/745 | (2015.01) | |
| A61K 35/747 | (2015.01) | |
| A61K 36/064 | (2006.01) | |
| A61K 36/235 | (2006.01) | |
| A61K 36/48 | (2006.01) | |
| A61K 39/00 | (2006.01) | |
| C12N 1/20 | (2006.01) | |

(52) U.S. Cl.
CPC ......... *A61K 35/744* (2013.01); *A61K 35/741* (2013.01); *A61K 35/742* (2013.01); *A61K 35/745* (2013.01); *A61K 35/747* (2013.01); *A61K 36/064* (2013.01); *A61K 36/235* (2013.01); *A61K 36/48* (2013.01); *C12N 1/20* (2013.01); *A61K 2035/115* (2013.01); *A61K 2039/521* (2013.01)

(58) Field of Classification Search
None
See application file for complete search history.

(56) References Cited

U.S. PATENT DOCUMENTS

| | | |
|---|---|---|
| 6,080,401 A | 6/2000 | Reddy et al. |
| 11,065,283 B2 | 7/2021 | Agrawal et al. |
| 11,077,052 B1 | 8/2021 | Reddy |
| 2012/0087902 A1* | 4/2012 | Rescigno ............ A61P 1/16 435/7.1 |
| 2016/0317637 A1 | 11/2016 | Agrawal et al. |
| 2018/0243347 A1 | 8/2018 | Agrawal et al. |
| 2019/0290706 A1 | 9/2019 | Biffi et al. |
| 2021/0290736 A1 | 9/2021 | Lugo et al. |
| 2022/0370520 A1 | 11/2022 | Biffi et al. |
| 2023/0190833 A1 | 6/2023 | Biffi et al. |

OTHER PUBLICATIONS

Torres-Fuentes et al. The FASEB J. 33: 13546-13559, 2019.*
Siciliano et al, Paraprobiotics: A New Perspective for Functional Foods and Nutraceuticals, Nutrients, Apr. 8, 2021, vol. 13 Issue 4, 1225; Download pages numbered 1-19, consider pp. 1-3. Downloaded Jan. 29, 2024 from https://doi.org/10.3390/nu13041225.
Taverniti et al, The immunomodulatory properties of probiotic microorganisms beyond their viability (ghost probiotics: Proposal of paraprobiotic concept). Genes & Nutrition, Apr. 16, 2011, vol. 6, pp. 261-274, consider p. 271 at "Conclusions." Downloaded Jan. 29, 2024 from https://doi: 10.1007/s12263-011-0218-x.

* cited by examiner

Primary Examiner — S. Devi
(74) Attorney, Agent, or Firm — Kyle W. Rost

(57) ABSTRACT

The therapeutic or healthful aspect of nutritional supplements, dietary supplements, and drugs has been significantly improved synergistically through infusion of paraprobiotics (inactivated or attenuated or killed probiotics) along with their immunomodulins or postbiotics, especially those of genus *Lactobacillus, Bacillus, Lactococcus, Pediococcus, Propionibacterium, Enterococcus, Streptococcus, Penicillium,* and *Brevibacterium*. The objection of using live probiotic bacteria as adjuvants in combination with the nutraceuticals, dietary supplements and drugs by the medical practitioners has been obviated through use of paraprobiotics along with their postbiotics to improve health or treat a specific disease.

6 Claims, No Drawings

ENHANCED MICROBIAL THERAPEUTIC AGENTS

CROSS REFERENCE TO RELATED APPLICATION

This application incorporates by reference herein in its entirety U.S. Pat. No. 6,080,401 filed Nov. 19, 1998, under Ser. No. 09/196,922 and issued Jun. 27, 2000.

FIELD OF THE INVENTION

The invention generally relates to therapeutic activity of chemical compounds or medicinal preparations and to microorganisms or materials there from. More specifically, the invention relates to microbes and to probiotics.

BACKGROUND OF THE INVENTION

The invention relates to bio-affecting nutraceuticals, dietary supplements, and drugs which are activated with the inclusion of paraprobiotics along with their postbiotics. More specifically the invention relates to replacing probiotics, which are live, with the same efficacy using inactivated paraprobiotics along with their postbiotics. Some instances, the inventions further relate to intentional mixture of two or more paraprobiotics of different genera to enhance the efficacy of dietary supplements, nutraceuticals, and therapeutic drugs. The invention relates to the use of nutraceuticals and dietary supplements to the improvement of certain aliments, and also pharmacotherapy (to treat or cure certain disease) in which the scope of medical preparations includes a range of pharmaceuticals include allopathic drugs, periodontal drugs, homeopathic drugs, Ayurvedic drugs, Siddha drugs, Unani drugs, and herbals drugs including but not limited to Chinese herbal medicines etc. There are several medicines available (in addition to the nutraceuticals and dietary supplements which are not considered drugs) in the marketplace, which are as follows: Ayurveda; Siddha; Unani; Chinese herbal medicine; herbal medicines; and homeopathy. Most of these medicines predominantly involve herbs as active ingredients. The mechanism, philosophy, and types of active ingredients used in each system are different. The details of these systems including the allopathic medicines are presented to differentiate them from each other.

Allopathic medicines—Allopathic medicines are individual active ingredients in beneficial herbs developed in the 18$^{th}$ century, leading into a transitional period from the use of natural herbs to the use of pharmaceutical drugs such as extracts and purified chemicals, sometimes referred to as allopathic drugs. The modern medicine practiced widely throughout the world is allopathic medicine. Although the allopathic drugs are fast acting and dosage-controlled therapeutics, they have a serious drawback of inducing unwanted side effects in some cases, which are much worse than their curative properties. If you look into television ads on allopathic medicines, the list of side effects is longer than their therapeutic effects. Close to or more than 30% of the diseases are due to side effects of the modern allopathic drugs, which includes both prescription as well as over the counter drugs. Allopathic medicine approach is basically a symptomatic treatment, addressing only symptoms rather than core cause of the disease, thus there are multitude of diseases which cannot be cured.

Ayurveda—It is an ancient traditional medicine, native to India, founded around 5000 years ago. Ayurveda follows the approach of 5 elements that our universe is made of. These elements are earth, water, fire, air, and space (ether). These five elements are represented in the human body as three doshas which are called Vata, Pitta, and Kapha. The unique combination of these doshas dictate the temperament and mental makeup of an individual. Each individual is born with a specific combination or percentage of these three doshas. This is called "Prakruthi" and it is specific to each individual. Due to altered food habits or environmental changes or influences, if the ratio or the percentage of three doshas vary (deviate from Prakruthi), it will result in "Vikruthi", and it will be manifested as disease. Thus, Ayurvedic medicine is aimed at strengthening the capacity of the body to fight disease through the use of specific herbs to restore the "Prakruthi" (the original ratio of Vata, Pitta, Kapha). The Ayurvedic treatment also includes special diets, massages, yoga, meditation, and cleansing techniques through Panchakarma therapy. Once again, the treatment modality of Ayurveda is to put the patient back to "Prakruthi" states to cure the disease. Unlike allopathic drugs, the Ayurvedic drugs are slow acting although they do not exhibit side effects.

Siddha medicine—It is a traditional medicine originated in South India (specifically in the Tamil Nadu). This is considered one of the oldest medical systems of India, involving the use of herbs, in-organic substances and animal products. The combination of 5 natural elements earth, water, fire, air, and sky (ether) dictates the composition of three humors in the body. Thus, Siddha emphasizes the fact that the three humors in the body, Vaadham, Pittam, and Kapam must be in ratio of 4:2:1, and any deviation of this established ratio will result in disease. The Siddha medical system believes that diet and lifestyle play a major role in maintaining health and curing diseases. The concept of Siddha medicine is termed as "Pathyam" and "Apathyam," which is essentially a role-based system of dos and don'ts, and it is principally related to specific food and diet to cure a disease. Although Siddha is extensively practiced in rural India, it is not yet recognized as official alternative medicine, like Ayurveda. Even these Siddha medicines are slow acting even though they do not exhibit any side effects.

Unani medicine—Unani founded in the teachings of Hippocrates with contributions from Greek philosophers Galen and Razes. It was developed into elaborate medical system by Arabs and Persians and is being practiced extensively in the Middle East and South Asian countries. Unani uses regimental therapy involving the process to eliminate toxic agents and cause cleansing of system through messages as well as through special diets, by regulating quality and quantity of food. Just like Ayurveda, Unani is also an approved alternative medicine, which has the greatest benefit (like Ayurveda) in prevention or curing the musculoskeletal disorders, respiratory diseases, skin diseases, and other chronic diseases, which allopathic medicines could not or failed to cure. Since the allopathic system is mainly practiced treating the symptoms rather than the core cause of disease, Unani and Ayurveda are getting popular as alternative as well as complementary alternative medicines. Unani medicines are made from natural substances of plant origin, specifically herbs. Unani also believes in 5 key elements of nature earth, water, fire, air and ether, which control the health of the human body, through control and proper maintenance of the four humors. The four humors are blood, phlegm, yellow bile, and black bile. The Unani practitioner diagnoses the disease predominantly by checking the pulse and also by considering the appearance of the person, sleep pattern, diet, and mental makeup etc. Thus, ultimately the treatment is aimed at balancing the 4 humors. Apparently, Unani medicine does not include inorganic and animal base products, and predominantly uses herbal products as therapeutic agents.

Homeopathic medicines—Although homeopathy has been considered as a pseudoscientific system of alternative medicine, it is very popular in several parts of the world. According to the survey Germans spend about 650 million euros per annum, and 2014 survey proved that 60% of the Germans use homeopathic medicines. In the year 2008, France spent about 460 million US dollars, and in the United States the amount spent on homeopathic medicines was close to $5 billion a year. In India, the homeopathic medicine is officially accepted as an alternative medicine, and it comes under the regulations of the Ayush Department. In this context, Ayush stands for Ayurveda, Unani, Siddha, and homeopathy.

The concept of homeopathic medicine was conceived and developed by German physician Samuel Hahnemann in 1796. The practitioners of homeopathic medicine believe that a substance that causes symptoms of a disease in healthy people can cure similar symptoms in sick people. This doctrine is called "similar similibus curentur," in simple terms it is "like cures like." These medicines are made using homoeopathic dilution technique, which includes serially diluting the medicament to the point that none of the original substances may be present in the final dilution. Yet, such a diluted medicament when adsorbed into a pill made of lactose sugar etc. and administered to a patient, cures the disease. Although it is belief driven, it is not science-based medicine, yet it is practiced extensively in several parts of the world. In this connection, homeopathic medicines also include herbs as part of the medicaments in addition to several inorganic compounds, depending on the ailments they are intended to cure.

Chinese herbal medicine—The Chinese herbal medicine is part of a larger healing system called Traditional Chinese Medicine (TCM). The TCM is around 2000 years old, and its basic concept is that a vital force of life, called Qi (pronounced as Chee), is spread, and distributed throughout the body. The Qi is made by opposite (yin) and complementary forces (yang). A perfect balance in yin & yang maintains Qi in the body to ensure a perfect health. Any imbalance due to alternation in the yin & yang ultimately causes imbalance in "Qi," which causes the disease and illness. The concept or belief behind the TCM is that humans are microcosms of the larger surrounding universe, and thus are interconnected with nature and are subjected to its forces. When the unity of such forces is disturbed, it manifests itself as disease, thus a balance between health and disease is a key concept. TCM treatment is designed to restore this balance to treat the disease.

According to TCM, to regain the balance one must achieve the balance between the internal body organs and the eternal elements of earth, water, fire, wood, and metal. One of the ways to regain and restore energy balance involves the use of herbal medicines, which can balance the yin & yang to perfectly maintain the vital force of life "Qi". The yin & yang imbalance is predominantly due to stress, pollution, infection, poor diet, and emotional upset. Chinese herbal medicines are mainly plant based and some preparations may include minerals or animal products. In the literature it is also stated that some herbs can be toxic in high doses and others may cause allergic reactions, and thus one has to be careful to select the herbs and their dosage.

The allopathic medicines although acts at a faster pace to cure the primary disease, they have serious drawback in that they cause side effects which are more severe than the primary disease. Furthermore, they cannot cure several chronic diseases. Turn around, the herbal medicines or nutraceuticals or dietary supplements involved in various alternative medicines (Ayurveda, Siddha, Unani, Chinese herbal medicine, homeopathy) are slow acting, even though they do not induce any side effects. U.S. Pat. No. 6,080,401 was a breakthrough in that the herbal medicines were made to act faster to cure a disease, through infusion of live probiotic bacteria belonging to several genera and species, without inducing any side effects. The discovery was also novel in that it was able to reduce the side effects of the allopathic and periodontal pharmaceutical drugs.

According to the World Health Organization (WHO) and Food and Agricultural Organization, the probiotics are defined as follows: Probiotics are live micro-organisms which when administered in adequate amounts confer a health benefit on host. This is the accepted and widely used definition which encompasses all applications of live microorganisms to improve health. The following are the commonly used probiotics which have been proven to have beneficial therapeutic effects upon administration: *Lactobacillus casei, Lactobacillus rhamnosus, Lactobacillus plantarum, Lactobacillus paracasei, Lactobacillus helveticus, Lactobacillus bulgaricus, Streptococcus thermophilus, Bacillus coagulans, Bifidobacterium bifidum, Bifidobacterium longum, Lactococcus lactis* subsp. *lactis, Lactococcus lactis* subsp *cremoris, Lactococcus lactis* var *Lactis* subsp *diacetylactis, Pediococcus acidilactici, Enterococcus faecium, Saccharomyces boulardi, Brevibacterium linens, Penicillium roquefortii, Penicillium camembertii, Propionibacterium shermanii, Propionibacterium arabinosum,* and *Propionibacterium jensenii* etc. All of these listed probiotics are considered GRAS (Generally Regarded as Safe), according to the United States Code of Federal Regulations of the Food and drug Administration (FDA).

According to the latest literature, some of the bacteria associated with intestinal microbiota also confer health benefits to humans. One such example is Akkermansia muciniphila, which constitutes 2 to 3 percent of the total gastrointestinal microbiota. There are several other bacteria which can improve human health, provided they are clinically proven to be safe.

The medical professionals and practitioners are objecting to the use of live probiotics as integral part of the drugs, (although they are very effective in enhancing drug activity with least or no side effects) (Siciliano et. al., Paraprobiotics: A new perspective for functional foods and nutraceuticals, nutrients, 2021, 13, 1225). The reasons are as follows: Probiotics when mixed with drugs under certain circumstances, may develop drug resistance due to mutation or through development of drug resistant plasmids (extrachromosomal genes), which can produce newer enzymes which may inactivate or alter the active principle of the drugs; drug resistant genes, from live probiotic bacteria can be passed on to several pathogenic bacteria which can cause nosocomial infections and also may lead to severe endemics, epidemics and pandemics. In addition, physicians fear administering live probiotic bacteria (even along with drugs) to the immunocompromised individuals, cancer patients (who have low white blood cells) etc. thinking they might not be safe. Also, the fear of using live probiotic bacteria which can disturb the natural composition of the microbiota leading to dysbiosis. Finally, the number of live probiotics over time may change the efficacy of drugs, causing inconsistency in treatment of ailment. (Taverniti et. al., the immunomodulatory properties of the probiotic microorganisms beyond their viability (Ghost probiotics; proposal of paraprobiotic concept), Genes Nutr. 2011, 6, 261-274).

Thus, to obviate the restrictions imposed by several medical and complementary alternative medical professionals around the world, the intent of the current discovery is to come up with a solution to eliminate the inclusion of live probiotics in the drugs, as outlined in U.S. Pat. No. 6,080,401, yet with similar functionality of enhancing the drug efficiency with least or no unwanted side effects. Perhaps such alternative is the use of paraprobiotics along with their therapeutic growth end products (postbiotics), if they can perform as good as live probiotics to enhance the supplement or drug efficiency. Paraprobiotics are inactivated (non-colony forming) probiotics. The commercially available probiotics have the highest number of bacterial cells with the least concentration of growth end products or postbiotics. However, in the current discovery, the applicant would like to include both the paraprobiotics and postbiotics to improve the efficacy of nutraceuticals or drugs. In practice, the paraprobiotics can also be prepared without their growth end products. Technically live probiotics have two major functions in improving health. One is competitive inhibition of pathogenic bacteria due to their innate ability to grow and outcompete them. Another is through induction of proper immunomodulation to improve the immunity of the host. Immune modulation is mainly controlled by the prior growth end products of probiotic bacteria. These are called immunomodulins or postbiotics, they are: Lactic acid, propionic acid, acetic acid, butyric acid, hydrogen peroxide, therapeutic peptides, bacteriocins, and non-specific therapeutic protein breakdown products and several short chain fatty acids etc. These immunomodulins or postbiotics activate the host lymphatic system to improve immunity through proper immunomodulation. In addition, the cell walls of live probiotics or dead probiotics (paraprobiotics), which have peptidoglycan, oligosaccharides, lipoproteins etc. also will have immunomodulating effect to activate the host lymphatic system. Yet so far there is no invention involving infusing paraprobiotics (inactivated probiotics) along with their prior growth end products (immunomodulins or postbiotics) into the nutritional supplements and drugs to enhance the drug efficiency, through synergistic effect. This concept, if proven through experiments and clinical trials, can eliminate the use of live probiotic bacteria and replace them with totally killed paraprobiotics along with their immunomodulins to accomplish the same task of enhancing therapeutic drug efficiency with least side effects.

In this connection it is worthwhile to point out the prior publications and inventions to distinguish and differentiate the novelty and non-obviousness of the current invention. They are as follows:

Lugo et. al. in the abstract of US Pub. No: US 2021/02090736 A1, specifically stated the following: "A composition or nutritional supplement containing undenatured type II collagen in combination with probiotic cell matter and/or prebiotic. The probiotic cell matter composition of Lugo et. al. is as follows: The probiotic cell matter and/or prebiotic materials themselves can comprise either a single probiotic organism, a probiotic component, or a prebiotic molecule, a mixture of two or more probiotic organisms, probiotic components, two or more inactivated probiotic organisms (i.e. paraprobiotics), or prebiotic molecules, or any combination of whatsoever of the above-mentioned embodiments (paragraph 0008, lines 22 to 28). It has to be noted that in Lugo et. al. invention probiotic cell matter involved both live probiotics and paraprobiotics and did not include their postbiotics (the soluble growth end products of either probiotics or postbiotics).

In paragraph 0013, (lines 1-8) Lugo et. al. stated that the probiotic cell matter also includes various different probiotic derivatives that may comprise mixtures of processed cell components of probiotic organisms, or mixtures of nutrients and one or more components derived from probiotic organism cells. For example, a probiotic derivative may comprise processed cell fractions that contain, for instance, metabolites, membrane components and hydrolysates. However, metabolites are not postbiotics, they are part of bacterial metabolism comprising both the primary and secondary metabolites. The primary metabolites are the intracellular molecules of life that enable growth and multiplication of the bacteria, whereas the secondary metabolites are extra cellular molecules that facilitate a microbe's interaction with its environment. Thus, both the metabolites belong to the cells but not as growth end products of the cells i.e., postbiotics. The membrane components of the cell and the cell hydrolysates are also integral parts of the cell, but not considered as postbiotics.

Thus, Lugo et. al. did not include postbiotics either with probiotics or paraprobiotics in their invention. Whereas, prebiotics are non-cellular and non-digestible food ingredients, and they have no connection with postbiotics, which are the soluble growth end products of probiotics. It is a customary practice in the industry to concentrate probiotic bacteria through centrifugation or ultrafiltration to eliminate the soluble growth end products i.e., postbiotics. Such concentrated cells are generally lyophilized and can also be used to make paraprobiotics.

In the applicant's current investigation, the paraprobiotics include all the soluble growth end products of the bacteria, including all the cell components and the metabolites etc. used in combination with either dietary supplements or nutritional supplements or the drugs to enhance their therapeutic efficiency synergistically.

Lugo et. al. also pointed out that the probiotic alone can be effective in combination with collagen to improve the joint function (paragraph 0031, lines 6 through 11). A mention has also been made stating that probiotic cell matter includes probiotic organisms, which include viable bacteria and yeast cells and paraprobiotics, which includes killed or inactivated cells of probiotic organisms (paragraph 0033, lines 1 through 7). Thus, Lugo et. al's invention involves both the live probiotics and the inactivated paraprobiotics, together called the probiotic cell matter. The main objective of applicant's current invention is to totally inactivate the probiotics (non-viable paraprobiotics) along with their growth end products (immunomodulins or postbiotics) and check their effect on improving the supplement or drug efficiency on reducing or curing a specific disease or disease symptom. Lugo et. al. has also mentioned that the probiotic organisms used as an ingredient of "probiotic cell mass" may comprise bacteria or yeast cells that have been treated or altered but remain viable. In the same paragraph it is also mentioned that the probiotic organism cells that have undergone heat treatment, but retain viability, may be used in accordance with the invention (paragraph 0039, lines 1 through 7).

It has been mentioned that the probiotic cell matter can also be replaced by a prebiotic. Prebiotics are non-digestible food ingredients that can either stimulate or support the growth of probiotics and thereby indirectly improve the joint health efficiency of Type-II collagen supplement or improve the joint health (paragraph 0043, line 1 through 8). Lugo et.

al. clearly admitted that the probiotic cell matter which has both viable probiotics and paraprobiotics can be replaced by a non-probiotic origin, non-digestible food ingredient (prebiotic). The applicant's current invention is to check the effect of totally inactivated (not viable at all) paraprobiotics along with their immunomodulins to improve the supplement or drug efficiency to cure a specific ailment. Under the section of claims (claim #5) of Lugo et. al., it is clearly stated as follows: "A method as defined in claim 1, wherein Type II collagen source is administered to the mammal in conjunction with the probiotic cell matter, and the probiotic cell matter comprises a probiotic organisms, a paraprobiotic, or a mixture thereof. Under the section of claims (claim #6), it is clearly stated as follows: A method as defined in claim #5, wherein probiotic cell matter comprises the probiotic organism, the probiotic organism comprising bacteria or eukaryotic organisms.

Furthermore claim #20 clearly states that Lugo's composition has the following live probiotics in the amount of one million CFU to 200 billion CFU (CFU-colony forming units, meaning the inclusion of live probiotics). Claim #29 also clearly states the following "a nutritional product as defined in claim #28, wherein the cell matter comprises the probiotic organism, the probiotic organism comprising a bacteria or a eukaryotic organism.

In another investigation, U.S. Pat. No. 11,065,283 B2 by Agrawal et. al., clearly states that the immunomodulatory compositions comprising live *Caulobacter crescentus* (CC), to modulate an immune response in an individual, involving administering an immunomodulatory composition comprising live CC to the individual (Abstract). Specifically, under the section of claims (claim #1) it is stated clearly as follows: "A method of treating an inflammatory disease, disorder, or a condition in an individual, the method comprising administering to the individual an effective amount of immunomodulatory composition, the immunomodulatory compound comprising: a) live *Caulobacter* species etc. This invention is limited to live *Caulobacter* species only. The invention of Biffi et. al. pub no: US 2019/0290706 A1, clearly stated that their invention relates to the composition based on bacteria and/or yeasts and/or other microorganisms, taken singularly or in combination for the treatment and symptoms of and/or for treating irritable bowel syndrome (IBS).

It also states that HKCC can be generated by exposing *Caulobacter crescentus* to a temperature of from 37° C. to about 95° C. for a time period of one minute to two hours, to make HKCC non-viable (paragraph 0069). The comment here is, how could you make paraprobiotics by heat treating at only 37° C.?

According to the Biffi et. al. pub no: US 2020/0306323 A1, their invention relates to the use of specific strains of *Lactobacillus paracasei* or of a composition comprising said strains for the prevention of and/or treatment of a physio pathological condition related to/associated with *Clostridium difficile* (CD) infection, preferably intestinal infections, or so-called CD associated disease (CDAD) or CD infection (CDI). Although they have mentioned definition of probiotics (Paragraph 0059), paraprobiotics (paragraph 0063), they have limited their use to probiotics only by themselves and they did not claim and mention of using paraprobiotics as an aid to improve the efficiency of specific drug and nutritional and/or dietary supplements. Paragraph 0069 specifically states the number of live bacteria to be included as a treatment aid i.e., up to 300 billion per administration.

Biffi et. al. (US Patent application publication No. US 2023/0190833A1, Pub. Date: Jun. 22, 2023) specifically mentioned that in their invention (paragraph 0082) having at least one bacterial strain preferably of the species *Lactobacillus paracasei* present in a composition comprised from 1 times 10 to the power six CFU/gram or ml to one times 10 to the power twelve CFU/gram. The compositions according to the present invention may comprise several different bacterial strains in several CFU ratios. It indicates that Biffi et. al., composition primarily was depending on the live probiotics in combination with vitamin D, to treat the vitamin D deficiency symptoms. The abstract of the invention and claim 1 clearly indicates that live probiotic bacteria were used along with vitamin D to prevent or treat vitamin D deficiency. In addition, claim 19 clearly states the following: The said bacterial strain is administered in association combined with vitamin D3, wherein said administration of said bacterial strain and of vitamin D is simultaneous or delayed over time.

In a separate investigation, Biffi et. al., (United States Patent Application Publication-Pub No: US 2022/0370529 A1-Pub. Date: Nov. 24, 2022.) mentioned that (in the abstract and in paragraph 0077) the composition includes probiotic bacteria (live and viable) and paraprobiotics or postbiotics. It further states that (paragraph 0077) the bacterial strains of the invention are the probiotic bacterial strains (live and viable organisms). The invention involves some form of live probiotics to enhance the effect of berries to be used as an immunomodulatory and anti-inflammatory agents (Abstract).

Biffi et. al., in another investigation (United States Patent Application Publication—Pub. No.: US 2019/0290706 A1, Pub. Date: Sep. 26, 2019.) clearly stated both in the abstract, as well as in paragraphs 0029 and 0032 as follows: The micro-organisms of the composition of the present invention are preferably alive and the composition therefore also defined as probiotics (paragraph 0029); the composition of the invention is also a probiotic or a paraprobiotic or a postbiotic. Biffi et. al., invention only involves the use of probiotics or paraprobiotics or postbiotics by themselves for treating abdominal pain and discomfort associated with irritable bowel syndrome (IBS). In addition, claim No. 6 states as follows: The method according to claim 1, wherein said bacteria are alive or dead, as lysate or extracts or fractions. Claim 8 clearly states that the bacteria are administered in a quantity ranging from one billion to one hundred billion of live bacteria for each administration. The invention is purely using either live probiotics or paraprobiotics or postbiotics by themselves to treat the symptoms of the irritable bowel syndrome (IBS) and did not use them in combination with supplements or drugs to enhance the supplement or drug efficiency.

Agrawal et. al., (United States Patent Application—Pub. No: US 2018/0243347A1—Pub. Date: Aug. 30, 2018.), specifically mentioned in the abstract, which is as follows: "The present disclosure provides immunomodulatory compositions comprising live *Caulobacter crescentus* (CC). Their disclosure thus provides methods of modulating an immune response involving administering an immunomodulatory composition comprising live CC to the individual." Thus, according to the invention it is very clear that live micro-organism is a must to induce the immune response.

Agrawal et. al., (US Patent Application Pub. No: US2016/0317637 A1.) claims that heat killed *Caulobacter crescentus* (HKCC) can be used as an ingredient in the immunomodulatory compositions. It is also stated that *Caulobacter crescentus* has been used as a carrier or delivery vehicle to deliver antigens, due to electrostatic and hydrophobic interactions, and bio adhesion/mucoadhesion (paragraph 0075).

It is clear that HKCC has been used as a carrier of the antigen derived of pathogenic microorganisms (claim #1) and not as an ingredient to synergistically enhance the effect of the immunomodulatory composition. In another paragraph (paragraph 0068) it is stated as follows: "An immunomodulatory composition of the present disclosure can comprise HKCC in an amount from $10^2$ to about $10^{20}$ CFU dosage form. A unit dosage form can be 0.5 Ml, 1.0 Ml for administration in a single dose.

It is a known fact in the trade that in order to get $10^{20}$ CFU (Colony Forming Units) the culture must be devoid of postbiotics or the soluble growth end products, since it has to be either centrifuged or ultra-filtered to get to such a concentration. While doing that, the soluble growth end products or postbiotics must be discarded as supernatants or filtrates. It is a well-known fact in commerce. Thus, upon their own admission, the HKCC is devoid of the soluble growth end products or postbiotics. Such a highly concentrated HKCC without their postbiotics must have been used as a carrier ingredient in the immunomodulatory composition, rather than a synergistic compound. It is also stated in the invention (paragraph 0069) that HKCC can be generated by exposing *Caulobacter crescentus* to a temperature of 37° C. to about 95° C. for a period of one minute to two hours, to make HKCC non-viable. At 37° C. temperature *Caulobacter crescentus* will be viable and thus cannot be considered as a paraprobiotic, but instead it can be called a probiotic.

None of the prior investigators have investigated the efficacy of using combinations of paraprobiotics along with their postbiotics, in combination with the supplements or drugs to enhance the therapeutic efficiency of supplements and/or drugs. The current invention of the applicant is first of its kind to overcome the objection of the medical community for not using live probiotics along with supplements or drugs.

SUMMARY OF THE INVENTION

One object of the invention is to enhance the therapeutic performance of a variety of therapeutic agents, to enable the result that a reduced quantity of the enhanced therapeutic agents will perform substantially equivalently to a previously specified dosage of the non-enhanced therapeutic agent. An advantage of this result is to reduce drug resistance.

Another object is to improve the therapeutic performance of therapeutic agents without requiring higher dosage.

According to the invention, an improved method for preventative or curative treatment has been achieved for relief from antibiotic side effects, anxiety, arthritis pain, depression, sore throat, and stamina deficiency. This is achieved by administering to a subject in need of such treatment a first preparation of a therapeutic agent, apart from a bacterial strain, in a preselected dosage of a first preparation that has a previously known efficacy at a previously established effective dosage for treating a selected disease, symptom, or disorder. The invention enables the preselected dosage of administration for the first preparation to be reduced from the previously established effective dosage of administration for the first preparation, or it simply enhances the known performance of the therapeutic agent. The invention achieves these results by substantially simultaneously administering to the subject a second preparation of an enhancing agent effective when administered in sufficient relative quantity to increase the efficacy of the combined first and second preparations to at least substantially equate with said previously known efficacy of the first preparation at the previously established dosage of administration for the first preparation. The second preparation is composed of a probiotic microorganism that is dead or in the form of a lysate, extract, or fraction of said probiotic microorganism; and a metabolic byproduct generated by a probiotic microorganism, and/or any other product of bacterial derivation. The second preparation is administered in quantity sufficient to increase the efficacy of the combined first and second preparations to at least substantially equate with said previously known efficacy of the first preparation at the previously established dosage of administration for the first preparation. It is understood that the concept of substantially equal performance is empirically determined by observation of patients in a comparative study.

Other diseases, symptoms, or disorders that the invention has been tested with are anemia, bacterial septicemia, cardiac deficiency, cholesterol, constipation, coronavirus related flu, diabetes, dyspepsia, gassiness, hay fever, hemorrhoids, hepatitis, hives, hypertension, impotency, memory loss, obesity, periodontal disease, and sleep deficiency.

The first and second preparations can be administered simultaneously in separate dosage units; or they can be administered simultaneously in a combined dosage unit. When using separate dosage units, administration at the same time might be within minutes or even longer, such as within an hour of each other. The goal is to ensure that the both dosage units are taken into the subject's system in a time frame allowing them to cooperate and interact. Where a first preparation is known to be fast-acting, the two dosage units should be administered very close to one another, such as within minutes.

The second preparations, which may be referred to as paraprobiotics and postbiotics, are derived from precursor probiotics. These may be probiotic microorganisms of the same strain, different strains, or mixed strains.

The relative quantity to be administered of the first and second preparations should be sufficient to achieve enhancement of the first preparation or an enhancement of the combined first and second preparations. The chosen relative weight of second preparation may be in a quantity from 0.01% to 90% of the combined weight of the first and second preparations.

The invention further provides a dosage unit of an enhanced therapeutic composition having efficacy in the treatment of a human or animal subject in need of such treatment for a disease, symptom, or disorder selected from antibiotic side effects, anxiety, arthritis pain, depression, sore throat, and stamina deficiency. The dosage unit is composed of a first preparation of non-enhanced therapeutic agent, apart from a bacterial strain, having a previously known efficacy in a previously established efficacious quantity for treating a selected disease, symptom, or disorder. The dosage unit is further composed of a second preparation of an enhancing agent effective when administered in sufficient relative quantity to increase the efficacy of the combined first and second preparations to at least substantially equate with said previously known efficacy of the first preparation at the previously established dosage of administration for the first preparation. The second preparation is a paraprobiotic of a precursor probiotic microorganism that is dead or in the form of a lysate, extract, or fraction of said precursor probiotic microorganism; and a postbiotic that is a metabolic byproduct generated by a precursor probiotic microorganism, and/or any other product of bacterial derivation. When the first and second preparations are combined, they form an enhanced therapeutic composition in the dosage unit, with the first and second preparations in relative quantities sufficient to provide an efficacy of the combined first and second preparations that at least substantially equates with said previously known efficacy of the non-enhanced therapeutic agent in the previously established efficacious quantity. This result enables the dosage unit to contain less than the previously established efficacious quantity of the non-enhanced therapeutic agent, while achieved the known result of administering the full previously known dosage for the non-enhanced therapeutic agent.

The precursor probiotic of the components of the second preparation can be chosen from *Streptococcus thermophilus, Propionibacterium shermanii*, and mixtures thereof. Other suitable precursor probiotics are *Lactobacillus acidophilus, Bifidobacterium bifidus, Bacillus coagulans, Saccharomyces boulardi*, and mixtures thereof. Other suitable genera are *Lactobacillus, Bacillus, Lactococcus, Streptococcus, Pediococcus, Propionibacterium, Brevibacterium, Penicillium, Saccharomyces*, and mixtures thereof.

The disease, symptom, or disorder to be treated by the dosage unit can be selected from anemia, anxiety, arthritis pain, cardiac deficiency, cholesterol, constipation, coronavirus related flu, decreased sex drive, depression, diabetes, gassiness, hay fever, hemorrhoids, hepatitis, hives, hypertension, impotency, memory loss, periodontal disease, sleep apnea, sore throat, and stamina deficiency.

The precursor probiotic of paraprobiotic in the second preparation is a cultured microorganism grown in a media of milk or milk derived ingredients. Likewise, the precursor probiotic of the postbiotic in the second preparation is a cultured microorganism grown in a media of milk or milk derived ingredients.

The first preparation of the dosage unit can be herbal, formed of herbs selected from fennel, fenugreek, and mixtures thereof.

The use of plural dosage units enables synchronized administration a therapeutic agent and an enhancing agent. The therapeutic agent has efficacy in the treatment of antibiotic side effects, anxiety, arthritis pain, depression, sore throat, and stamina deficiency. A first dosage unit of the plural dosage units contains a first preparation of therapeutic agent, apart from a bacterial strain, wherein the first preparation has a previously known efficacy when administered in a previously established efficacious quantity for treating the selected disease, symptom, or disorder. A second dosage unit of said plural dosage units contains a second preparation of an enhancing agent effective to increase the efficacy of the therapeutic agent. The second preparation contains a paraprobiotic that is dead or in the form of a lysate, extract, or fraction of a precursor probiotic microorganism. The second preparation also contains a postbiotic that is a metabolic byproduct generated by a precursor probiotic microorganism, and/or any other product of bacterial derivation. The first and second preparations are combined by synchronized administration to the subject of the first and second dosage units in relative quantities sufficient to provide an efficacy of the combined first and second preparations that at least substantially equates with the previously known efficacy of the first preparation in its previously established efficacious quantity. A desired result is that the first dosage unit is enabled to contain less than said previously established efficacious quantity of the therapeutic agent.

Plural dosage units are applied for treatment of anemia, bacterial septicemia, cardiac deficiency, cholesterol, constipation, coronavirus related flu, diabetes, dyspepsia, gassiness, hay fever, hemorrhoids, hepatitis, hives, hypertension, impotency, memory loss, obesity, periodontal disease, and sleep deficiency.

The second dosage unit is of a weight range from 0.01% to 90% of the combined weight of the first and second dosage units.

DETAILED DESCRIPTION OF THE INVENTION

The current objection of using live probiotics along with the supplements and/or drugs to enhance their preventative or therapeutic effects has been obviated by totally replacing live probiotics with their paraprobiotics with the inclusion of postbiotics, to enhance the preventive or therapeutic effects of supplements and/or drugs through series of experiments and clinical trials outlined in the following sections.

This invention is two-fold 1. Enhancement of the activity of nutraceuticals or dietary supplements with the infusion of paraprobiotics (inactivated probiotic) and their postbiotics to assist or support the health of the individuals; 2. Enhancement of drug activity of specific drugs belonging to herbal medicine, Ayurvedic medicine, Unani medicine, Siddha medicine, homeopathic medicine, periodontal medicine, and allopathic medicine, by combing with paraprobiotics and their postbiotics to cure or treat a specific disease due to enhanced drug values, without inducing any adverse side effects. Although U.S. Pat. No. 6,080,401 (Reddy et. al, U.S. Pat. No. 6,080,401, Date of Patent Jun. 27, 2000) teaches that the drug activity can be enhanced with a combination of live probiotics and drugs to treat or cure disease, with no side effects, several medical practitioners and drug manufactures have been objecting to the use of live probiotic micro-organisms along with the drugs due to several reasons, which were outlined earlier. Similar objection was also raised to not combine the nutraceuticals or dietary supplements with live probiotic micro-organisms due to variance in efficacy due to long-term storage. The physicians' objection is because of the unknown effect of live probiotic micro-organisms (even though they are beneficial to a healthy individual) on the immunocompromised individuals or individuals with cancer and other chronic disease etc. and also organ transplant individuals who are treated with immune suppressant drugs.

Thus, the current invention involves paraprobiotics (inactivated probiotics), along with their immunomodulins or growth end products or postbiotics to replace the live probiotics, as outlined in U.S. Pat. No. 6,080,401 of Reddy et. al. The invention involves two stage of contraction: In the first, nutraceuticals or drugs are formulated and prepared which can assist the health of the individual (as former) or to cure or treat the disease (as later), and in the second, the efficiency of nutraceutical (dietary supplement) or drug activity is enhanced by selecting and adding suitable paraprobiotics (inactivated probiotic micro-organisms) along with their growth end products or immunomodulins or postbiotics to the nutraceuticals or drugs. U.S. Pat. No. 6,080,401 has utilized probiotics which are non-pathogenic, non-toxin producing, beneficial culture preparations belonging to the genus *Lactococcus, Lactobacillus, Pediococcus streptococcus, Propionibacterium, Brevibacterium, Penicillium* and *Saccharomyces* and mixtures thereof. The discovery of Reddy et. al., (U.S. Pat. No. 6,080,401) specifically mentioned and used only live probiotic bacteria to blend with specific drugs and did not mention the use of any paraprobiotics to enhance the drug efficiency to cure diseases at a faster pace, without inducing any unwanted deleterious side effects. According to their discovery, the synergistic effect was due to drugs (specifically herbals), acting as prebiotics and live micro-organisms as probiotics. Accordingly, the resultant symbiosis greatly improved the drug efficiency.

However, the current inventions are aimed at using inactivated or dead probiotics (paraprobiotics) along with their growth end products or immunomodulins or postbiotics in combination with drugs to improve the drug efficiency significantly, due to some other biochemical mechanism, since the probiotics are not live. Thus, the term paraprobiotics in this connection is referred to as, previously grown probiotics which are induced to produce more growth end products or immunomodulins or postbiotics, and then inactivating or attenuating or killing the live probiotic bacteria to arrive at paraprobiotics. The invention is serendipitous in that unexpectedly even the paraprobiotics along with their growth end products or postbiotics in combination with the drugs resulted in enhancing the drug efficiency to treat or cure the specific disease, without any side effects, proving that the probiotics do not have to be live to improve the drug efficiency. Similar observations were made to enhance the effect of nutraceuticals or dietary supplements by mixing with the paraprobiotics along with their growth end products.

In this connection, a single herb (ashwagandha or turmeric or basil or clove) or multiple mixed herbs can be categorized as nutritional supplements, provided their intent is not to cure, diagnose or treat a specific disease. Similarly, probiotics can be categorized as dietary supplements as long as they are not intended to be used as drugs to cure, treat, or diagnose a disease. Thus, use of single herb or multiple mixed herbs when mixed with paraprobiotics along with their growth end products (postbiotics) can be categorized as either nutraceuticals or dietary supplements. Turn around, the therapeutic herbs when mixed with paraprobiotics, which have significant effect to cure a disease and thus, declared as a drug has to go through drug approval process. However, the same preparation can be categorized under nutraceutical or dietary supplement, if it is not claimed as drug, provided the ingredients used are GRAS (Generally Regarded as Safe) and the disclaimer states that these products are not intended to diagnose, treat, cure, or prevent any disease. In addition, one can add to the label stating that, "these statements have not been evaluated by the Food and Drug Administration." According to the above disclaimer, any herbal preparation belonging to Ayurveda, Unani, Siddha, or Chinese herbal medicine can be categorized under nutritional supplements, provided it is not claimed as drug, since they are botanicals. The use of paraprobiotics is safer because the live probiotic bacteria is inactivated or killed to eliminate the skepticism by the medical community on the use of live probiotic bacteria for certain patients.

The following definitions outline the principle and philosophy behind different medical modalities referred to in this patent application.

Herbal or a natural drug includes a medicinal preparation administered most commonly in approximately the state or concentration as found in nature, such as by ingesting a leaf, stem, root, flower, seed, pollen, node, hip, or the like. Thus, and herbal drug principally is of plant origin can be categorized under this category. It includes Ayurveda, Siddha, Unani, Chinese herbal medicine etc.

Allopathy is a method of treating diseases by the use of agents that produce effects different from those of the disease treated and it is mostly symptomatic treatment, rather than curing the sole cause of disease. Allopathy is generally considered to be modern medicine and allopathic drugs are considered to be pharmaceutical drugs as described in pharmacopoeia. The allopathic drugs could be extractions of purified versions of the herbal drugs, while others may be chemical and biological compositions not otherwise found in nature. Antibiotics also come under allopathic medicines. It is well established that allopathic drugs, although fast acting, will induce severe adverse side effects.

Homeopathy is a variety of medicine that treats disease by giving drugs in minute quantities prepared using serial dilutions. However, the substances or drug ingredient administered may be, in some cases similar to dilute versions of herbal or allopathic medicines. The efficacy of homeopathic drugs is also questioned due to lack of evidence-based research.

A periodontal drug is a remedy applied to the mouth or gum tissue, such as toothpaste, tooth powder or floss, to effectively control bacteria and decay.

Diet drugs or weight loss drugs are intended to make a person lose weight, which was caused due to multiple metabolic disorders. Currently abnormal weight or obesity is considered as a disease.

U.S. Pat. No. 6,080,401 teaches that in order for the drugs to be activated with the infusion of probiotics, the probiotic micro-organisms must be live. Also, it did not consider the necessity of having the growth end products of the live probiotic bacteria (postbiotic) to be incorporated along with drugs, to enhance the drug activity. In some cases, the patent specifically mentioned to spin the culture to concentrate the live probiotic bacteria, to totally eliminate the growth end products or immunomodulins or postbiotics in the dried probiotic preparation to be mixed with the drugs, to enhance the drug efficiency. Apparently, the invention was relying heavily and predominantly on using live probiotic bacteria only to activate the herbs or drugs through symbiosis. However, the current discovery relies on using the paraprobiotics (inactivated or dead or non-colony forming probiotic bacteria along with their growth end products or postbiotics) to be mixed with either nutraceuticals and/or drugs, to enhance their efficacy, through synergy or interactions, either to support the health conditions or to treat a disease at a much faster pace, without any side effects.

The current invention of the applicant, due to inclusion of specific paraprobiotics along with the postbiotics with the nutraceuticals or dietary supplements or drugs to enhance their efficiency, results in using less amount of the nutraceutical or therapeutic dose intended either to support the health or treat a disease condition at much faster pace, without any adverse side effects. It is always good to reduce the amount of usage or dosage of drugs to eliminate their toxic effects. Such reduction in usage of the therapeutic drugs has been achieved serendipitously in the current applicant's invention.

Selection and preparation of nutraceuticals is as follows:

Nutraceuticals: The herbal nutraceuticals intended to be used to improve or support the general health, immunity, and overall wellness are selected on the basis of their established physiological functions. Thus, single herbs such as ashwagandha or basil or turmeric etc. have been prepared or purchased from commercial sources. Most of these preparations are concentrates of herbs and did not have any microbial contaminants. The dosage and amounts of herbs are standardized on the basis of the percentage of the active principle in the concentrate. Under certain circumstances, herbs were also prepared using the procedure outlined in U.S. Pat. No. 6,080,401. The non-herbal nutraceuticals are prepared using the food grade or pharmaceutical grade ingredients, to be blended with paraprobiotics along with their postbiotics to support or improve the overall health or specific health condition.

Herbal drugs: Herbal drug formulas with specific ingredients and range of ingredients are formulated on the basis of herbal properties. The herbs used in these preparations are mostly concentrated extracts with at least minimal or no bacterial contaminants (including saprophytic or pathogenic bacteria, virus, yeast, and molds). Since we were evaluating the efficacy of improving the drug activity without using the live probiotics, most of the herbal drug formulations were prepared with similar compositions outlined in the U.S. Pat. No. 6,080,401. In addition, several commercial herbal formulations, homeopathic formulations, and supplements with different compositions and functions were purchased in the finished form to blend with the paraprobiotics along with their postbiotics to check the improved efficacy of these supplements, in accordance with this invention. The popular commercial herbal formulations such as SHA1 PLUS, and commercial homeopathic formulations such as HISTAMINUM 30 C and HEMCALM were included in the experimental studies.

The following probiotics (which were used to make paraprobiotics along with their immunomodulins) were used or mentioned in the current formulations. To eliminate the redundancy, only the additional probiotics that are used in this discovery, but not listed in the U.S. Pat. No. 6,080,401 are only listed along with their therapeutic functions. They are as follows:

1. *Lactobacillus helveticus*: It is a probiotic bacterium which is acid and bile resistant and thus can survive stomach acid and bile to reach the small intestinal tract. It has wide range of potential benefits such as reducing blood pressure, arthritis, and allergies; maintaining the optimum composition of intestinal microbiota, improving bone health, and decreasing anxiety and depression.
2. *Bifidobacterium longum*: It is a probiotic organism that in combination with *Lactobacillus helveticus* reduces anxiety, depression, and stress related cognitive dysfunction. It is a multifunctional probiotic with a specific function of microbiota and microbiome modulation to orchestrate the physiological activities of gut associated micro-organisms. It alleviates gastro-intestinal, immunological, and infectious diseases.
3. *Lactobacillus rhamnosus*: It is one of the most widely used probiotics to treat or prevent the gastro-intestinal infections, to stimulate immune response that promotes vaccinations, and to prevent certain allergies. It has exceptional ability to interact with a host due to its inherent Lipoteichoic acid molecules, its secreted proteins, and its galactose rich exopolysaccharides.
4. *Lactobacillus plantarum*: It is a gram-positive lactic acid bacterium with a myriad of therapeutic effects due to its antioxidant, anti-diabetic, anti-obesity, anti-inflammatory, and anti-cancer properties. It has been used in the treatment of Alzheimer's, Parkinson's, diabetes, obesity, hypertension, liver disorders, and urogenital complications.
5. *Lactobacillus casei*: It is another popular lactic acid producing probiotic bacteria which has intrinsic ability to decrease metabolic endotoxemia by altering the gut flora composition and gut permeability. It also improves neutrophil function and insulin resistance in obesity since gut flora seems to play an important role in the development of inflammation and metabolic syndrome in obesity.
6. *Lactobacillus paracasei*: It is a homofermentative lactic acid bacteria and is genotypically and phenotypically closely related to probiotic *Lactobacillus rhamnosus*, It inhibits pathogenic *salmonella* and gastric cancer etiological biological agent *Helicobacter pylori*. It is very effective in treating ulcerative colitis and allergic rhinitis.
7. *Saccharomyces* boulardi; It is a popular yeast probiotic which has been used extensively to treat diarrhea associated with antibiotics and prevent diarrhea in people with feeding tubes. In addition, it has also been used to treat irritable bowel syndrome (IBS), inflammatory bowel syndrome (IBD), and colitis, lactose intolerance, vaginal yeast infections, and hypercholesterolemia.
8. *Propionibacterium freudenreichii*: Although it has a significant probiotic function, it also serves as a prebiotic to stimulate the growth of bifidobacterial species in the GI tract. In addition, it has been credited with lowering the incidence of colon cancer. It grows well in the presence of probiotic *Lactobacillus helveticus*.

The following herbals were used or mentioned in the current formulations. To eliminate the redundancy, only the herbs that are not listed in the U.S. Pat. No. 6,080,401 are listed along with their botanical names, common names, and their established therapeutic functions. They are as follows:

1. *Citrus sinensis* (Sweet orange). Limonene is the main chemical component present, which has antibacterial effect mostly on gram positive bacteria and antifungal activity. It has a strong antioxidant and free radical properties due to phenolic compounds, specifically flavonoids.
2. *Eucalyptus globulus* (*Eucalyptus*). Cineole is the active compound in *eucalyptus* oil, and it is used to improve respiratory functions and cough associated with the common cold or flu and to relieve symptoms or localized muscle pain. It has natural antimicrobial and antiseptic properties.
3. *Coriandrum sativum* (Coriander). It is a rich source of ascorbic acid, calcium, magnesium, manganese, iron and phytonutrients. Its health benefits include the reduction of skin inflammation, maintaining cholesterol levels and blood sugar levels in the blood; and reducing mouth ulcers, anemia, and indigestion. It has disinfectant, antiseptic, antifungal, antioxidant, and anti-microbial properties.
4. *Camellia sinensis* (tea). The catechins (flavonoids) are the primary active compounds in tea. It has antioxidation properties and also has an effect on preventing type-1 diabetes and reducing the fatigue. In addition, it is rich in B-vitamins, linoleic and alpha-linoleic acids and minerals including calcium, iron, zinc, magnesium, and selenium.
5. *Lavendula* sp (Lavender). It has strong antioxidant properties, and it is used to reduce anxiety, fight free radicals, and fight insomnia.
6. *Rosmarinus officinalis* (Rosemary). It has several phytochemicals such as caffeic acid, camnosic acid, chlorogenic acid, monomeric acid; oleanolic acid, rosemarinic acid, ursolic acid, alpha pinene, camphor, carnosol, and eucalyptol. It has antioxidant and anti-inflammatory properties, reduces physical and mental fatigue; produces an antiangiogenic and neuroprotective effect; reduces atherosclerosis; has antiviral, anti-cancer, anti-depressant, antimicrobial, hepatoprotective, nephroprotective, and antimutagenic properties, and reduces lipid peroxidation in heart and brain.

7. *Carum copticum* (Thyme). This herb has glucosides, saponins, phenolic compounds (carvacrol), volatile oils (thymol), and terpenes. It exhibits antifungal, antibacterial, antiparasitic, and hypolipidemic effect, and it reduces fatigue, respiratory distress, and abdominal tumors.

8 *Origanum vulgare* (Oregano). The main therapeutic components of this herb are carvacrol and thymol which are antibacterial. In addition, it has anti-inflammatory properties to reduce autoimmune arthritis, rheumatoid arthritis, and allergic asthma; and to protect against some cancers.

9. *Citrus bergamia* (Bergamot). It has flavonoid phytochemicals such as neoeriocitrin, naringin, neohesperiden, ponceritin, melitidin, mitrocin, miriflin, and brutieridinc, and it reduces cholesterol and lipids in the case of hyper lipidemia.

10. *Mentha arvensis* (Spearmint). The active compound in *Mentha arvensis* are menthol, menthone, isomenthone, neomenthol, limonene, methyl acetate, piperitone, beta-caryophyllene, alpha-pinene, beta-pinene, tannins and flavonoids. It is used for treating colds (antiviral) and for improving digestion. In addition, it is antibacterial with an intrinsic capacity to improve digestion. In addition, it is antibacterial with high potency to inhibit pathogenic Streptococci and Lactobacilli associated with dental problems.

11. *Syzygium aromaticum* (Clove). The main component of clove is eugenol and minor components include acetyleugenol, beta-caryophyllene, vanillin, crategolic acid, bicornin, gallotannic acid, methyl salicylate, eugenin, kaempferol, rhamnetin, and triterpenoids such as oleanolic acid, stigmasterol, campesterol, and several sesquiterpenes. Its main therapeutic function is analgesic used in dental practice. It has significant antioxidant, antimicrobial, antiviral, and antifungal properties mainly due to eugenol and other ingredients.

12. *Mentha piperata* (Peppermint). The therapeutic component of mentha peppermint is menthol. Other compounds include menthyl acetate, menthofuran, 1,8, cineol, limonene, pulegone, caryophyllene, and pinene. It is used in the treatment of irritable bowel syndrome, muscle and nerve pain, and itching.

13. *Cinnamomum verum* (Cinnamon). The active compounds in cinnamon are polyphenols, antioxidants, cinnamaldehyde, cinnamic acid, and cinnamate. It has the following therapeutic effects: Improves blood sugar regulation (anti-diabetic), improves insulin sensitivity, anti-bacterial (inhibits *E. coli* and *salmonella*), prevents neurological disorders (dementia etc.), prevents cell damage due its antioxidant and anti-inflammatory property, acts as prebiotic to regulate the optimal composition of gut microbiota, helps to prevent colon cancer, and prevents tooth decay and bad breath by being antibacterial.

14. *Azadirachta indica* (Neem). The main active therapeutic compound of *Azadirachta indica* is azadirachtin. Other minor components are nimbolinin, nimbin, nimbidin, nimbidol, sodium nimbinate, salanin, gedunin and quercetin. It has immunomodulatory, anti-inflammatory, anti-hyperglycemic, anti-ulcer, anti-malaria, anti-fungal, anti-bacterial, anti-viral, antioxidant, anti-mutagenic and anti-carcinogenic properties. It is used to treat inflammation, infections, fever, skin diseases and dental disorders.

15. Cymbopgon citrates (Lemon grass). The major constituents of lemon grass are neral, citral, and geranyl acetate. It is used to treat stomachache, high blood pressure, convulsions, cough, rheumatism, fever (antibacterial), common cold (antiviral), exhaustion, and digestive tract spasms.

16. *Nigella sativa* (Blackseed). The major therapeutic ingredients of *Nigella sativa* are linoleic acid, oleic acid, palmitic acid, trans-anethole, nigellicine, nigellidine, thymoquinone, carvacrol, thymol and various alkaloids. It is helpful in treating diabetes, autoimmune disorders, hypertension, asthma, inflammation, high cholesterol, eczema, psoriasis, and acne.

17. *Coccus nucifera* (Coconut). The coconut oil has medium chain fatty acids (MCTs). Lauric acid makes up 50% of the fatty acids as a therapeutic ingredient. It is helpful in improving heart health and reducing obesity. It is antibacterial, antiviral, and antifungal, reduces seizures, protects skin-hair-teeth, and improves brain function.

18. *Saccharum officinarum* (Sugar cane). The following are the phytoconstituents of sugar cane: wax, leaves, stalks, and sugar cane juice: various fatty acids, alcohol, phytosterols, higher terpenoids, flavonoids, glycosides and phenolic acids. Sugar cane juice is widely used to treat jaundice, dysuria, anuria, other urinary disease, and hemorrhage.

19. *Zea mays* (Corn). Acts as antioxidant due to the presence of phenolic compounds. It is used for improving the skin health to reduce acne, and reduce stress.

The probiotics that are made inactive are called paraprobiotics. The above specified probiotics were made into paraprobiotics, and they were used along with their postbiotics with specific drugs, nutraceuticals or dietary supplements to see if the paraprobiotics have similar functionalities as the probiotics to enhance their efficiency to cure a disease or to improve general health or a specific health condition, without having to induce any side effects. In this connection, I would like to elaborate and differentiate probiotics from paraprobiotics. The latest definition by the United Nations Food and Agricultural Organization (FAO) and the World Health Organization (WHO) along with the Canadian Research and Development Center for Probiotics, is as follows: Probiotics are any live micro-organisms which when administered in adequate amounts confer a health benefit on host. The following are the list of proven health benefits of probiotics: reduction of lactose intolerance, prevention and treatment of hospital acquired infections, improvement of longevity (anti-aging), reduction of viral infections, traveler's diarrhea and rotavirus diarrhea; reduction of intestinal bacterial infections, reduction of certain cancers; reduction of obesity, irritable bowel syndrome, autoimmune diseases, autism, constipation, and Parkinson's disease; reduction of serum cholesterol and triglycerides; reduction of hypertension and heart disease, reduction of allergies, reduction of *Helicobacter pylori* infections, improvement of immunity through immunomodulation, reduction of coronaviral infections, and reduction of osteopenia and osteoporosis etc.

If you analyze all the research conducted on probiotics to be used as therapeutic agents, it is quite obvious that the probiotic bacteria must be alive. The live probiotics have therapeutic properties and have synergistic effects on drugs to enhance their effect on curing the diseases at a faster rate, with no side effects, has been outlined in U.S. Pat. No. 6,080,401. Yet several medical practitioners and other health professionals are not in favor of using the live micro-organisms (probiotics) to administer to their patients, since all of the probiotics do not have immense health benefits, and in addition some of them are proven harmful to human health. Also, under certain circumstances specifically in immune compromised individuals, organ transplant patients, certain cancer patients whose white blood cell counts are significantly low, several physicians are reluctant to use live probiotics. In addition, patients who are on antibiotic therapy are discouraged from blending probiotics with antibiotics due to fear of creating antibiotic resistant probiotic bacteria, which can pass on the resistant genes to other pathogenic bacteria. Finally, the physicians are reluctant to use live probiotics due to reports showing that some probiotics may cause probiotic sepsis, pro-inflammatory response, serious infection such as septicemia, pneumonia, and scare to feed preterm neonates, due to lack of clinical studies. Although the validity of such observations is questionable, the skepticism induces fear in the minds of advocating physicians and health professionals.

To obviate the above suggested draw backs and objections of using live probiotics, the applicant has undertaken a mission to check if the inactivated probiotics along with their growth end products (immunomodulins) perhaps have similar health benefits in conjunction with drugs, like live probiotics, as outlined in the U.S. Pat. No. 6,080,401, to improve the drug efficiency with no adverse side effects or skepticism.

Paraprobiotics are nothing but killed or inactivated probiotics. Contrary to the definition of probiotics being live micro-organisms, paraprobiotics are inactivated or attenuated or dead probiotic bacteria. Limited research conducted mostly in vitro, and animal studies proved that some of the paraprobiotics of genus *lactobacillus* also have therapeutic effects. However, none of the prior investigations were conducted to see if paraprobiotics (which are completely inactivated) along with their immunomodulins also have any synergistic effect when incorporated along with the drugs or nutraceuticals or dietary supplements, to enhance their therapeutic or biological efficiency to cure disease or to assist in improving the general health, without any side effects. Literature is loud and clear in that the therapeutic effects of probiotics are genus, species, and strain specific, indicating that there are significant biological and molecular variations among several members of probiotics. Apparently, it is linked to their genome, the composition of their cell walls and the biochemical aspects of their growth end products, which may vary depending upon the nutrients present in the growth medium.

The U.S. Pat. No. 6,080,401 did specify that certain strains of live probiotics can only be mixed with compatible drugs to achieve the maximum benefit to cure a specific disease at a much faster pace, without any side effects. However, the effect of paraprobiotics (inactivated probiotics) along with their postbiotics under such circumstances, had never been investigated. In the case of probiotics, the definition specifically calls for the live microbial cultures in adequate amounts, yet there is no mention of their quantity or level of growth end products. In general, it is a common practice in the industry to concentrate the probiotic bacteria to arrive at maximum numbers of cells. It can be accomplished either through centrifugation or ultra-filtration. In both the systems, the growth end products of the probiotic bacteria (immunomodulins or postbiotics) are discarded. Thus, most generally, concentrated probiotic cultures will have least or no growth end products and they are freeze dried. The growth end products of probiotics are organic acids (lactic, acetic, propionic), proteolytic and lipolytic enzymes, therapeutic peptides, bacteriocins, molecular hydrogen peroxide, short chain fatty acids and other soluble non-specific stimulatory factors.

If the probiotic culture is not concentrated through centrifugation or filtration, it will have all the growth end products, and it is very difficult to freeze dry such large volumes. Thus, most of the time the probiotic growth end products are eliminated. The other reason is that the growth of end products will reduce the viability of live probiotics, which is not preferred in commerce, and will obviate the high concentration of live probiotic bacteria. Considering the above, the paraprobiotics are preferred to live probiotics, as long as they still have the therapeutic benefits and have synergistic effect to enhance the drug activity.

Paraprobiotics are defined as inactivated microbial cells or cell fractions that confer health benefit to the host. According to this definition the growth end products of the microbial cells are not categorized under paraprobiotics. However, they are categorized under the term postbiotics. Thus, postbiotics are defined as soluble products or metabolites secreted by probiotics that have physiological benefits to the host. In simpler terms the inactivated probiotic cell structure components (mainly the cell wall components not including their growth end products) are termed as paraprobiotics and the secretory metabolites/components other than cell structural components are termed as postbiotics. In order for the paraprobiotics to be effective during the production of paraprobiotics from probiotics, it is important to expose the cells to factors without disrupting the cell structure. In our study, for the sake of simplicity, paraprobiotics and postbiotics are together termed paraprobiotics with postbiotics, implying the inactivated probiotics along with their growth end products (postbiotics). Also, the paraprobiotics are prepared in such a way not to disrupt the majority of their cell walls, through selection of the growth medium and the selection of the growth conditions.

Paraprobiotics consist of wide range of molecules (in varying amounts depending or strains) including peptidoglycan, teichoic acid, cell wall polysaccharides, cell surface proteins, S-layer proteins, bacterial DNA, pili proteins, and moonlighting proteins.

Postbiotics consist of specific secreted proteins and peptides, and non-specific small molecules. The secreted proteins and peptides include protein P40 and P75; aggregation promoting factor (APF), and bacteriocins. The small molecules include short chain fatty acids, conjugated linoleic acid (CLA), and neurotransmitters. The best way to summarize is that the paraprobiotics are not water soluble and are mainly inactivated bacterial cells, whereas the postbiotics are predominantly soluble bacterial growth end products, which are excreted.

Our investigation revealed that the probiotics can be replaced with paraprobiotics (paraprobiotics along with their postbiotics). We have discovered that inclusion of both paraprobiotics and their postbiotics have significant effect on improving the efficiency of drugs, nutraceuticals, and dietary supplements, similar to live probiotics, provided a proper and selective growth medium is used. The experiments also proved that postbiotics when included also have some drug enhancing effect, compared to drug by itself.

Following are the physiological and therapeutic functions of the components of paraprobiotics and postbiotics.
Paraprobiotics:
1. Peptidoglycan—cell walls of bacteria contain a thick peptidoglycan layer, which is a multilayer cross linked glycan chain with repeating pentapeptide unit of B 1,4 linked N acetylglucosamine and N acetyl muramic disaccharide units. The composition of the glycans is specific and thus may vary from probiotic to probiotic, depending on which genus and species they belong to. This is the reason for using multiple mixed strain probiotics as effective therapeutic agents, rather than a single strain probiotic. Peptidoglycan suppresses inflammation provoking interleukin-12 (IL-12) production via toll-like receptor-2 (TLR), which has been associated with inflammatory bowel diseases and autoimmune diseases. Even the purified peptidoglycans exert anti-inflammatory properties by inducing IL-10 production. Peptidoglycan also stimulates dendritic cells and T-regulatory cell functions. In addition, it will stimulate and improve innate and systemic adaptive immune systems. However, the function of peptidoglycans to induce immunomodulation is strain specific and thus multiple mixed strain paraprobiotics is the way to induce optimal immunomodulation.

2. Teichoic acid—It also exerts anti-inflammatory effect through attenuation of IL-8. It is covalently bonded to peptidoglycan and the cytoplasmic membrane by their lipid anchors as lipoteichoic acid.

3. Cell wall polysaccharides—These are exopolysaccharides which help to mediate adhesion properties of paraprobiotics or probiotics to protect against pathogens. They also act as protective layers and modulate the systemic and mucosal immune responses. In addition, they exhibit immune-suppressive effect on macrophages by inducing high levels of IL-10 and low or no levels of TNF-alpha, IL-6, and IL-12. They also decrease the production of inflammatory cytokines, such as IL-6, IL-8, and MCP-1, under certain circumstances. They also exhibit antiviral effect by inducing the production of IFN-Y (interferon gamma) and natural killer cells (NK). They also help to decrease triglycerides and cholesterol in the blood. In addition, it has been proven that they inhibit tumor angiogenesis and thus protect the host from cancer.

4. Cell surface proteins—These proteins play a significant role in host biological process. These surface proteins include, S-Layer proteins, pili proteins and moonlight proteins. These proteins are attached to microbial cell surfaces through covalent or non-covalent bonds. The S-layer proteins can specifically inhibit adherence and infection of pathogenic bacteria. They also trigger the maturation of antigen presenting cells. pili proteins decrease the production of proinflammatory cytokines. They exhibit immunoregulatory function by interacting with monocytes and dendritic cells. They protect the intestinal epithelial cells from radiological effects. Moonlighting proteins include various classes of proteins including translational elongation factors, metabolic enzymes, ribosomal proteins, and molecular chaperones. These moonlighting proteins mediate the colonization of probiotic strains in the intestinal tract.

Postbiotics: Postbiotics are different secretory probiotic bacteria components which include proteins, organic acids, and other small molecules. The secreted proteins include protein P40 and P75. These proteins exert immunomodulatory action to reduce inflammation. P40 and P75 proteins protect the intestinal epithelial tight junctions and barrier functions. Aggregation-promoting factors (APF) are also secreted proteins of the probiotic bacteria which help to colonize probiotics in the GI tract and also inhibit adhesion of pathogens by competitive exclusion or by Co-aggregation with pathogens. Bacteriocins are ribosomal synthesized small antimicrobial agents with bactericidal or bacteriostatic effect on various pathogens. In addition, they also improve host immunity through immunomodulation through response of dendritic cells (DCs). They also improve the phagocytic activity of macrophages. They also improve the immune function of the host by selectively competing with specific bacterial strains and thus help to maintain the microbiota composition.

Irrespective of other soluble postbiotics, the small molecules are not strain specific and yet help to mediate the functions of probiotics. They include short chain fatty acids, conjugated linoleic acid (CLA) and various neurotransmitters. The short chain fatty acids serve as an energy source to colonic epithelial cells, regulating T-regulatory cells, anti-inflammatory effects, and intestinal permeability, and reduce colon cancer. Conjugated linoleic acid (CLA) has antitumor effect specifically on colonic, skin, mammary and prostate carcinogenesis in animal models. Probiotics contribute to proper functioning of gut-brain axis by producing neurotransmitters, such as Y-amino butyric acid (GABA), glutamate, serotonin, dopamine, norephrine, histamine, and acetylcholine. Thus, they confer beneficial health effects on mental health by acting as "psychobiotics." In addition, these neurotransmitters also reduce sleep related disorders, anxiety, and depression. Similar functions can be attributed to postbiotics.

In summary the beneficial effects of paraprobiotics or postbiotics are mediated through an interaction between the microbial products and host. These paraprobiotics and postbiotic components are recognized by pattern recognition receptors (PRRs), which further induce downstream signaling cascades that confer the beneficial functions to the host.

To date, nobody investigated the effect of paraprobiotics and the postbiotics, or postbiotics only in combination with drugs or nutraceuticals or dietary supplements on improving their efficiency to cure or treat diseases at a faster pace without any side effects or to assist in improving the general health and treating certain ailments in humans and animals.

Since this invention involves Ayurveda, Unani, Siddha, and homeopathy, which are controlled by Ayush Department of India, the probiotic and paraprobiotics cultures have to be made in accordance with the rules and regulations pertaining to those medical controlling departments. Thus, the lactic acid producing probiotics were grown in whole milk or skim milk or reconstituted whole or skim milk powders. The procedure for growing cultures in milk is as follows: Whole milk or skim milk is heated to 170° F. and held at that temperature for 30 to 45 minutes, with agitation. Then the milk is cooled to 75° to 115° F., depending upon the optimal growth temperature of the intended probiotic culture to be grown. For example, mesophilic lactic cultures prefer to grow at an optimal temperature of 75° to 90° F. Thermophilic lactic cultures prefer to grow at 100° to 115° F. Accordingly, the milk grown mother cultures are inoculated into the heat-treated milk and incubated until pH comes down 5.3 to 5.5. At that stage the growing culture is neutralized using either an automated external pH control system or a manual one or multiple step neutralization to maximize cell numbers and the growth end products. The neutralizing compounds used can be ammonium hydroxide or sodium/potassium hydroxide or calcium oxide/calcium carbonate. After attaining proper growth (which can be checked under direct microscopy), the culture is cooled to 40° F. This is referred to as a probiotic culture. In order to prepare a paraprobiotic culture (before cooling to 40° F.), the culture is neutralized to pH 6.0 and then heated to 160° to 180° F. to inactivate the live culture. This is called the paraprobiotic of that particular probiotic culture. Thus, both the live probiotic culture as well as inactivated paraprobiotic culture will have their growth end products intact. These growth end products alone, without the bacterial cells are termed as postbiotics. In other words, both the live probiotic cultures, as well as the inactivated paraprobiotic cultures will have their own postbiotics.

At this stage, the liquid probiotic cultures, as well as the paraprobiotic cultures, separately were mixed with food grade non-fat dry milk to make a doughy mass, and then they were dried at 27° to 37° F., until they became powder. This powder was milled and stored at 4° C., until used in medical or nutraceutical or dietary supplement or herbal preparations, in accordance with particular medical authority regulations.

Alternatively, to make paraprobiotic, the milk culture after second heat treatment (to inactivate probiotics), can be homogenized, condensed, and spray dried to make a spray dried paraprobiotic culture along with its own growth end products (postbiotics).

In order to use the probiotics or paraprobiotics in either dietary supplements or drugs where there are no stringent regulations are applicable, the following procedure is used to prepare probiotic as well as paraprobiotic cultures: The dry blended probiotic bacterial growth medium (the composition of which is presented in Table A) is reconstituted at 15% solids, heat treated to 175° to 190° F. and held for 45 to 60 minutes (with agitation), cooled to 78° to 115° F. (depends on the type of lactic acid producing probiotic to be cultured), inoculated with the proper culture and incubated until pH comes down to 5.0 to 5.5 and neutralized to pH 6.3 to 6.5 either using an automated external pH control system or a manual one or multiple step neutralization, until all the culture is fully grown. The neutralizing compounds can be gaseous ammonia, ammonium hydroxide or potassium hydroxide or calcium oxide.

At this stage, the culture is divided into three fractions. Fraction-I is called probiotic culture (along with its own postbiotics). It is fortified with the dry medium solids (as outlined in Table A) to arrive at 30% final solids. It is then either freeze dried or dried at 28° to 37° C. or spray dried at low temperature to prepare the probiotic culture. Fraction-II is used to prepare postbiotics by centrifuging the culture, to remove the probiotic bacteria. After centrifugation the supernatant is adjusted to 6.0 to 6.5 pH and then heat treated to 170° F. The heat-treated supernatant is condensed to 30% solids through evaporation and then spray dried. This is referred to as postbiotic. Fraction-III is fortified using the dry starter media (composition as outlined in Table 1), to arrive at 30% solids, and then heat treated to 170° F. It is then spray dried to make the paraprobiotic (along with its own postbiotics). Conversely, rather than spray drying, the mass can either be freeze dried or dried at 27° to 38° C. after heat treatment, to arrive at the powdered paraprobiotic preparation.

The probiotic *Propionibacterium* cultures were grown using the food grade sodium lactate broth. The broth was sterilized at 121° centigrade for 15 minutes at 15 pounds pressure. After sterilization, it was cooled to 21° to 25° centigrade and inoculated with appropriate probiotic *Propionibacterium* culture and incubated for 7 to 10 days. Then it is divided into three fractions. Fraction-I (both bacteria and their growth end products) was mixed with inert carrier such as corn flour or rice flour to make a doughy mass and then either freeze dried or dried at 27° to 38° C., until it becomes powder. Such powder is designated as dried probiotic *Propionibacterium*.

Fraction-II is pH adjusted to 6.5 and then heat treated to 170° to 180° F. to make *Propionibacterium* paraprobiotic culture. The rest of the procedure is same as its fraction I, to make the dried paraprobiotic *Propionibacterium*.

Fraction-III is centrifuged after heat treatment, to separate propionic acid bacteria from its growth end products. The supernatant is further heat treated to inactivate any residual bacteria, then made into powder using the similar procedure as fraction-I. This fraction-III powder is designated as postbiotic of the probiotic *Propionibacterium* culture.

Food grade probiotic (*Penicillium roquefortii* and *Penicillium camembertii*) were grown on moistened bread at room temperature. After the completion of their growth (observed visually), they were pulverized and were designated dried probiotics mold cultures. To make the paraprobiotic mold culture, the pulverized powder is reconstituted to 50% solids in water and heat treated to 170° F. to inactivate the live mold. The mass is then dried at 28° to 38° C. until it becomes powder. This is designated as mold paraprobiotic.

The probiotic yeast cultures were grown in food grade yeast extract fortified whey broth, with aeration. After the completion of growth, they were divided into two fractions. Fraction-I was fortified with inert corn or rice flour to arrive at 50% solids and then dried at 28° to 35° C. until it became powder. This is designated as probiotic yeast culture.

Fraction-II was heat treated to 170° to 180° F. to inactivate the yeast culture, and then it is made into powder using the same procedure as applied in faction-I. Fraction-II's inactivated yeast culture, along with its growth end products, is designated as yeast paraprobiotic.

In addition, the purchased commercial cultures were checked for purity with the aid of microscopy and biochemical characteristics. The culture preparations made to use in this investigation were prepared in accordance with the rules of Ayurveda, Siddha, Unani, herbal and other medical regulations in addition to Kashrut, and Halal rules and regulations and applicable certifications.

TABLE A

Growth medium for growing probiotic lactic acid producing bacteria

| Ingredient | Percentage | Typical range | Preferred range |
| --- | --- | --- | --- |
| Sweet whey | 53% | 35-70 | 45-60 |
| Non-fat dry milk | 15% | 5-330 | 10-20 |
| Autolyzed yeast extract | 10% | 3-12.5 | 5-11 |
| Disodium phosphate | 3.5% | 2-6 | 3-5 |
| Monosodium phosphate | 2% | 1-3 | 2-4 |
| Dextrose | 15% | 7.5-20 | 10-12.5 |
| Ferrous sulphate | 0.2% | 0.1-0.75 | 0.05-0.3 |
| Manganese chloride | 0.1% | 0.01-0.40 | 0.05-0.3 |
| Magnesium sulphate | 0.2% | 0.1-0.5 | 0.25-0.4 |
| Cellulose | 1.0 | 0.5-1.25 | 0.75-1.50 |

Thus, the probiotic as well as paraprobiotic cultures and postbiotics prepared using the aforementioned procedure were mixed with the nutraceuticals or dietary supplements or herbals or herbal drugs or allopathic medicines to study their efficacies to improve the activities of such supplements or drugs.

A similar composition of the growth medium outlined in Table A was prepared by replacing the milk derived ingredients, sweet whey and non-fat-dry milk with the rice flour, additional hydrolyzed soy protein solids and glucose to check for growth patterns and variance (if any) in the enhancement of the therapeutic efficiency of the nutraceuticals, dietary supplements, and drugs by such paraprobiotics, in comparison to the ones grown in growth medium with the inclusion of the milk based ingredients. To prepare the paraprobiotics and postbiotics separately, when non-fat-dry milk was used in the composition of growth medium outlined in Table A, the following procedure was followed. After the completion of the growth of probiotic strain, the cultured medium, the probiotics were inactivated by heating, while circulating using a centrifugal pump to make a smooth emulsion. To this smooth emulsion (pH 5.8) sodium citrate was added (in quantum sufficient-preferably around 1 to 2 percent) and further recirculated using the centrifugal pump until the culture mass was clear and translucent. Then the translucent culture mass was passed through a bactofuge to segregate the heat inactivated probiotic bacteria from their growth end products, i.e., postbiotics or immunomodulins. The postbiotics were dried using an inert carrier to arrive at the powdered postbiotics. These postbiotics were used in the subsequent experiments to check their effect on improving the efficacy of the dietary supplements and/or nutritional supplements and/or therapeutic drugs. Similarly, the paraprobiotics, (without the growth end products) were also dried. When the milk solids were replaced by non-milk solids, the step of using sodium citrate was eliminated, since the media was transparent and thus can be passed through the bactofuge to prepare both the paraprobiotics and the postbiotics. To prepare paraprobiotics along with their immunomodulins, the step of separating them using a bactofuge was eliminated, since it was not required. These preparations were included into the ENERGIMAC formula presented in Table 1, to check for their effect on enhancing (individually) the efficiency of a dietary supplement.

The following examples further illustrate the composition utility and method of preparing the products of this invention.

Example 1—A dietary supplement is formulated to help improve overall stamina and energy level. It is named as ENERGIMAC and the composition of which is presented in Table 1. The combined effect of probiotics or paraprobiotics (separately) with the ENERGIMAC formulation to significantly improve overall stamina and energy level has been studied using ENERGIMAC by itself as a control. Earlier U.S. Pat. No. 6,080,401 specifically dealt with drug compositions to treat certain ailments using drugs and probiotics together to enhance drug activity, without any side effects. The patented invention did not talk about the effect of specific paraprobiotics or paraprobiotics along with their postbiotics or postbiotics themselves on improving the functional efficacy of nutraceuticals or dietary supplements to improve the overall health.

In this connection, a definition of nutraceutical is a food or food component that claims to have health benefits, including treatment and prevention of disease. In 1989, Stephen DeFelice, M. D., derived the term nutraceuticals from "nutrition" and "pharmaceutical." The definition of dietary supplement, as defined by Congress in the dietary supplement health and education act, which became law in 1994, is a product that is intended to supplement the diet; contains one or more dietary ingredients (vitamins, minerals, herbs, amino acids, and other substances); is intended to be taken orally; and is labeled on the front panel as being a dietary supplement. The nutraceuticals differ from dietary supplements in that they help with disease prevention and treatment. Theoretically, the appeal of nutraceuticals has to do with accomplishing treatment goals without any side effects. Most generally both the terms, i.e., dietary supplements and nutraceuticals, are interchangeable because of very fine and subtle differences.

According to the above definitions, ENERGIMAC is categorized under dietary supplement and its composition is presented in Table 1. To check the effect of probiotics, paraprobiotics and postbiotics individually, the ENERGIMAC formula was used as base. In addition, ENERGIMAC without any probiotics, ENERGIMAC with probiotics, ENERGIMAC with paraprobiotics and postbiotics and ENERGIMAC with postbiotics served as positive controls. Probiotics, paraprobiotics, and postbiotics by themselves served as negative controls. All seven dietary supplement variables were tested on individuals whose energy levels and general stamina were low. This study was conducted under the supervision of qualified physicians and nutritionists. Each individual was asked to take one capsule in the morning and one capsule in the evening, continuously for a period of two months. The results are reported both in the one month and two months period. The results of the clinical trials are presented in Table 1. The results revealed that dietary supplement ENERGIMAC by itself has improved general stamina and energy level. However, ENERGIMAC combined with probiotics and ENERGIMAC combined with paraprobiotics had significantly improved the overall stamina and energy levels compared to ENERGIMAC by itself. The ENERGIMAC with postbiotics exhibited similar results as ENERGIMAC by itself. The interesting fact is that even though the percentage of ENERGIMAC (500 mg.) was significantly low in the combination of ENERGIMAC+ postbiotics, the efficacy was similar to the ENERGIMAC (750 mg/capsule) by itself, indicating that even the postbiotics had exhibited synergy with the dietary supplement to enhance its physiological properties. The subjects who were on probiotics, paraprobiotics, and postbiotics by themselves had the least effect on the first month and improved slightly on the second month. The results indicate that probiotics, paraprobiotics and postbiotics all have synergistic effect when mixed with ENERGIMAC to improve the efficiency of the dietary supplement, although the probiotics and paraprobiotics had much significant effect.

Additionally, the results of these experiments revealed that the probiotics and paraprobiotics used in this study were significantly more effective when they were grown with the inclusion of milk solids in the growth medium. Apparently milk or milk derived ingredients have unknown intrinsic properties to improve growth as well as the composition or intrinsic structure of the probiotic cell mass including their membrane integrity and intracellular and extracellular enzymes including permeases etc. When the probiotic cultures were grown in growth medium with the inclusion of the milk or milk derived ingredients and then prepared as paraprobiotics, the milk ingredients somehow improved the physiological characteristics of the probiotics, perhaps due to stimulation of the inducible enzymes controlled by plasmids.

The proximate composition of the ENERGIMAC is presented in Table 1. However, it is proven beyond doubt that the growth medium must have milk-based ingredients to significantly improve the efficiency of the paraprobiotics as well as their immunomodulins. This is a serendipitous observation which has a great significance to produce the best paraprobiotics. Thus, in our investigation we have used either complete milk-based ingredients or milk derived ingredients along with other bacterial stimulants to grow the probiotics to prepare the subsequent best effective paraprobiotics along with their postbiotics or immunomodulins. The results of the experiment are presented in Table 2. The results of the experiment presented in Example 1 distinctly proved that live probiotics can be replaced by inactive paraprobiotics along with their immunomodulins to enhance the effectiveness of the dietary supplements, to override the objection of physicians to including live probiotics even in dietary supplements and drugs. In addition, the dosage of the dietary supplement can be reduced by 33% by using the paraprobiotics along with their postbiotics, in combination with the dietary supplement, with greatly improved efficiency.

TABLE 1

The Composition of Dietary Supplement-ENERGIMAC

| Ingredient | Preferred percentage quantity (mg) per capsule | Typical range (mg) | Preferred range (mg) |
| --- | --- | --- | --- |
| Whey protein concentrate | 25.25 | 20.0 to 30.0 | 18.0 to 28.0 |
| Whey solids | 25.0 | 18.0 to 28.0 | 15.0 to 22.0 |
| Non-fat dry milk | 10.0 | 7.5 to 15,0 | 6.0 to 12.0 |
| Bioavailable calcium and all other major and minor milk minerals | 10.0 | 5.0 to 12.0 | 4.0 to 8.0 |
| Autolyzed yeast extract | 10.0 | 5.0 to 12.0 | 6.5 to 8.0 |
| Magnesium sulfate | 0.25 | 0.15 to 0.75 | 0.25 to 0.60 |
| Manganese chloride | 0.25 | 0.15 to 0.75 | 0.25 to 0.60 |
| Multivitamins | 2.0 | 0.50 to 5.0 | 0.25 to 4.0 |
| Inulin | 2.25 | 1.5 to 5.0 | 1.0 to 4.0 |
| Fructo-oligosaccharide | 2.25 | 1.5 to 5.0 | 1.0 to 4.0 |
| Hydrolyzed soy solids | 10.0 | 5.0 to 15.0 | 6.0 to 12.0 |
| Cellulose | 2.00 | 1.0 to 3.0 | 1.5 to 2.5 |

TABLE 2

Effect of ENERGIMAC (dietary supplement), with or without inclusion of probiotics, with or without inclusion of paraprobiotics (along with their postbiotics), or with or without inclusion of postbiotics, and their effect on improving overall stamina and energy level.
CODING: (−) Bad*, (+) Slight improvement, (++) Better, (+++) Excellent.

| Variables and quantity/capsule | Symptoms after one month administration | | | Symptoms after two months administration | | |
| --- | --- | --- | --- | --- | --- | --- |
| | Overall stamina | Energy level | Side effects | Overall stamina | Energy level | Side effects |
| ENERGIMAC - 750 mg | ++ | ++ | **ND | +++ | ++ | ND |
| ENERGIMAC - 500 mg + ***probiotics - 250 mg | ++ | +++ | ND | +++ | +++ | ND |
| Probiotics only - 750 mg | + | − | ND | + | + | ND |
| ENERGIMAC - 500 mg + ***Paraprobiotics - 250 mg | ++ | +++ | ND | +++ | +++ | ND |
| Paraprobiotics only - 750 mg | + | − | ND | + | + | ND |
| ENERGIMAC 500 mg + *****postbiotics - 250 mg | ++ | ++ | ND | ++ | ++ | ND |
| Postbiotics only - 750 mg | −− | −− | ND | −− | + | ND |

*Symptoms before administration:Overall stamina (−), energy level (−)
**ND - None detected
***Probiotics used in equal proportion of 20:20:20:20:20: Live *Bacillus coagulans*, *Bacillus subtilis*, *Lactobacillus helveticus*, *Lactobacillus rhamnosus*, and *Streptococcus thermophilus*, along with their growth end products.
****Paraprobiotics used in equal proportion of 20:20:20:20:20: Inactivated *Bacillus coagulans*, *Bacillus subtilis*, *Lactobacillus helveticus*, *Lactobacillus rhamnosus*, and *Streptococcus thermophilus*, along with their growth end products.
*****Postbiotics are growth end products of the above listed probiotics, without any live or inactivated paraprobiotic bacteria.

Example 2—The enhancing effect of nutraceutical basil (herbal extract) with or without inclusion of probiotics, paraprobiotics and postbiotics individually was evaluated to improve the general health, sexual activity, and reduction of anxiety. Since a single herb (extract) has been used as a therapeutic supplement, this formula can be categorized under nutraceutical as opposed to the dietary supplement. Probiotics only, paraprobiotics only, and postbiotics only served as negative controls. All the seven variables as outlined in Table 3, were tested clinically under the supervision of physicians. The test subjects were asked to take two capsules per day for 2 hours before going to bed, continuously for a period of two months. The results were tabulated and presented in Table 3. The results, presented in Table 3, clearly indicate that basil plus probiotics and basil plus paraprobiotics significantly improved the efficacy of basil to improve general health, sexual activity, and reduction of anxiety. Even the postbiotics included with nutraceutical (basil) exhibited similar effect as higher concentration of basil indicating that postbiotics also have some synergistic effect to improve the efficiency of nutraceutical. However, the synergistic effect is significantly higher with the paraprobiotics along with their postbiotics. The results clearly proved that live probiotics can be replaced with inactive paraprobiotics along with their postbiotics and to lesser extent with postbiotics only (if required) in combination with the nutraceuticals. In this example also, we have discovered that growth medium with inclusion of the milk solids was far superior to the medium without milk solids.

Example 3—The improved efficiency of most commonly used therapeutic herbs, in Siddha medical practice "neem" as nutraceutical, by inclusion of specific probiotics, paraprobiotics, and postbiotics had been evaluated. The preparations with probiotics, paraprobiotics, and postbiotics only served as negative controls. The seven composition variables included in this example along with the clinical results are presented in Table 4. The patients were asked to take 1 capsule in the morning and on capsule in the evening for a period of two months. The results of this trial were tabulated by physicians. The results of this trial proved that nutraceutical neem plus paraprobiotic was significantly better than neem plus probiotic and neem itself. The variable neem plus postbiotic also exhibited improved efficiency in comparison to neem only. Thus, proving the live probiotics can be replaced by inactive paraprobiotics and also postbiotics in the composition having neem as a major ingredient in the nutraceutical formulation, to improve general health, wound healing, and reduction of arthritis pain, without any side effects. The inactive paraprobiotics performed better in the nutraceutical formula than probiotics perhaps due to slight inhibitory effect of neem on live probiotics. This example also proved that paraprobiotics or postbiotics can be used along with therapeutic herbs which have inhibitory effect on live probiotics. This experiment clearly proved the superiority of using paraprobiotics along with their postbiotics in comparison to probiotics alone. Since some of the herbs will have inhibitory effect on the probiotics, it is highly advisable to use paraprobiotics along with their postbiotics to improve the efficacy of the nutraceutical.

TABLE 3

Composition of nutraceutical therapeutic herb basil with or without inclusion of probiotics, with or without inclusion of paraprobiotics (along with their postbiotics), or with or without inclusion of postbiotic, and their effect on improving general health, reduction of anxiety, and improvement in sexual activity.
CODING*: (−) Bad, (+) slight improvement, (++) better, (+++) excellent

| Variables and quantity/capsule | Symptoms after 1 month Administration | | | Symptoms after 2 months Administration | | |
|---|---|---|---|---|---|---|
| | General Health | Reduction of anxiety | Improvement in sexual activity | General Health | Reduction of anxiety | Improvement in sexual activity |
| Basil - 750 mg | + | + | + | ++ | + | ++ |
| Basil - 500 mg + **Probiotics - 250 mg | ++ | + | + | +++ | +++ | +++ |
| Probiotics only - 750 mg | + | + | − | ++ | + | + |
| Basil - 500 mg + ***Paraprobiotics - 250 mg | ++ | ++ | + | +++ | +++ | +++ |
| Paraprobiotics only - 750 mg | + | + | − | ++ | + | + |
| Basil - 500 mg + 250 mg Postbiotics**** | + | + | + | ++ | ++ | ++ |
| Postbiotics only - 750 mg | + | + | − | ++ | + | + |

*Symptoms before administration: General health (−); Anxiety (−); Sexual activity (−)
**Probiotics used: Live *Lactococcus lactis subsp cremoris* (33%), *Lactobacillus plantarum* (33%), and *Lactobacillus rhamnosus* (33%), along with their growth end products.
***Paraprobiotics used: Inactivated *Lactococcus lactis subsp cremoris* (33%), *Lactobacillus plantarum* (33%), and *Lactobacillus rhamnosus* (33%), along with their growth end products.
****Postbiotics are growth end products of the above listed probiotics, without any live or inactivated paraprobiotic bacteria.

TABLE 4

Composition of nutraceutical therapeutic herb "neem" (predominantly used in Siddha medicine practice) with or without inclusion of probiotics, with or without inclusion of paraprobiotics (along with their postbiotics), or with or without postbiotics, and their effect on improving general health, improving wound healing, and assisting to reduce pain associated with arthritis.
CODING: (−) Bad*, (+) - slight improvement, (++) - better, (+++) - excellent*

| Variables and quantity/capsule | Symptoms after 1 month administration | | | Symptoms after 2 months administration | | |
|---|---|---|---|---|---|---|
| | General Health | Wound healing | Reduction of Arthritis pain | General Health | Wound healing | Reduction of Arthritis pain |
| Neem - 750 mg only | + | + | − | ++ | ++ | + |
| Neem - 500 mg + **Probiotics- 250 mg | ++ | ++ | + | +++ | ++ | +++ |
| Probiotics - only 750 mg | + | − | − | + | − | − |
| Neem - 500 mg + Paraprobiotics - 250 mg | ++ | ++ | ++ | +++ | +++ | +++ |
| ***Paraprobiotics only - 750 mg | + | − | + | + | − | + |
| Neem - 500 mg + 250 mg Postbiotics**** | + | + | + | ++ | ++ | ++ |
| Postbiotics only - 750 mg | + | − | − | + | − | − |

*Symptoms before administration:General health (−); Wound healing (−); Arthritis pain (−)
**Probiotics used in equal proportion of 50:50: Live *Bacillus coagulans* and *Pediococcus acidolactici* along with their growth end products.
***Paraprobiotics used in equal proportion of 50:50: Inactivated *Bacillus coagulans* and *Pediococcus acidolactici* along with their prior growth end products.
****Postbiotics are growth end products of the above listed probiotics, without any live or inactivated paraprobiotic bacteria.

Example 4—The enhancing therapeutic effect of probiotics, paraprobiotics, and postbiotics on improving the efficacy of nutraceutical ashwagandha to improve general health, to reduce pain, to reduce anxiety and depression has been studied. The composition of seven nutraceutical variables to study their therapeutic effects are presented in Table 5. The patients were selected by the physicians, and they were asked to take 2 capsules per day, continuously for a period of two months. The results were tabulated using the data obtained on the first month and second month.

The results proved that ashwagandha concentrate fortified with probiotics, paraprobiotics, and postbiotics (individually) had exhibited similar results on improving the general health, reduction of pain, reduction of anxiety and depression. However, they have significantly improved efficacy in comparison to ashwagandha only. The negative controls used the probiotic only, paraprobiotic only, and postbiotic only, without ashwagandha, and did not have any significant effect in comparison to ashwagandha only, indicating that probiotics, paraprobiotics, and postbiotics have synergistic effect to improve the therapeutic effect of ashwagandha, without any side effects. It is proven that live probiotics can be replaced by paraprobiotics or postbiotics in combination with nutraceuticals, with equal efficiency as live probiotics. Apparently, in this example both the probiotics and paraprobiotics exhibited similar enhancing effect on the nutraceutical. It once again proves that paraprobiotics along with their immunomodulins are the better choice to add to the nutraceuticals to satisfy the physicians who are objecting to using the live probiotics to some of their patients. In addition, one does not have to worry about the inhibition of the probiotics by a specific nutraceutical. Here also it is proven that with the inclusion of paraprobiotics along with their postbiotics, the concentration or the amount of ashwagandha can be reduced by 33 percent in the nutraceutical formulation.

TABLE 5

Composition(s) of nutraceutical single herb ashwagandha with or without inclusion of probiotics, with or without inclusion of paraprobiotics (along with their postbiotics), or with or without postbiotics, and their effect on improving general health, reduction of pain, and reduction of anxiety and depression.
CODING: (−) Bad*, (+) slight improvement, (++) better, (+++)excellent

| Variables and quantity/capsule | Symptoms after 1 month administration | | | Symptoms after 2 months administration | | |
|---|---|---|---|---|---|---|
| | General Health | Reduction of pain | Reduction of anxiety & depression | General Health | Reduction of pain | Reduction of anxiety & depression |
| Ashwagandha - 750 mg (without Probiotics) | + | + | + | ++ | + | + |

TABLE 5-continued

Composition(s) of nutraceutical single herb ashwagandha with or without
inclusion of probiotics, with or without inclusion of paraprobiotics (along with their
postbiotics), or with or without postbiotics, and their effect on improving general health,
reduction of pain, and reduction of anxiety and depression.
CODING: (−) Bad*, (+) slight improvement, (++) better, (+++)excellent

|  | Symptoms after 1 month administration | | | Symptoms after 2 months administration | | |
| --- | --- | --- | --- | --- | --- | --- |
| Variables and quantity/capsule | General Health | Reduction of pain | Reduction of anxiety & depression | General Health | Reduction of pain | Reduction of anxiety & depression |
| Ashwagandha - 500 mg + **Probiotics - 250 mg | ++ | ++ | ++ | +++ | ++ | ++ |
| Probiotics only 750 mg | + | − | + | + | − | + |
| Ashwagandha - 500 mg + Paraprobiotics - 250 mg | ++ | ++ | ++ | +++ | ++ | ++ |
| ***Paraprobiotics - only - 750 mg | + | − | − | + | + | + |
| Ashwagandha - 500 mg + 250 mg Postbiotics**** | ++ | ++ | ++ | +++ | ++ | ++ |
| Postbiotics only - 750 mg | − | − | − | + | − | + |

*Symptoms before administration: General health (−); pain (−); anxiety and depression (−).
**Probiotics used in equal proportion of 50:50: *Lactobacillus acidophilus* + *Bifidobacterium bifidus*, along with their growth end products.
***Paraprobiotics used in equal proportion of 50:50: Inactivated *Lactobacillus acidophilus* + along with their prior growth end products.
****Postbiotics are growth end products of the above listed probiotics, without any live or inactivated paraprobiotic bacteria.

Example 5—The inclusion of probiotics, paraprobiotics, and postbiotics with turmeric (used as nutraceutical) on improving the therapeutic effect of turmeric on general health, reduction of pain, and reduction of anxiety and depression in patients. It had been evaluated by undertaking through clinical trials. The probiotics, paraprobiotics, and postbiotics by themselves (without turmeric) served as negative controls. The participating patients were asked to take 2 capsules per day, continuously for a period of two months. The physicians were asked to physically interview the patients after one month and two months periods, during the clinical study period and code the data, including any side effect.

The results are presented in Table 6. The results clearly proved in this example showing that turmeric plus paraprobiotic fared much better than turmeric plus live probiotics, although they both were significantly better than turmeric by itself. Turmeric plus postbiotic also gave better results than turmeric by itself indicating there is synergistic effect to improve the efficiency of turmeric even by the postbiotics. Also, the paraprobiotics (without turmeric) have exhibited better therapeutic effect than the live probiotics (without turmeric) indicating the optimal therapeutic abilities of paraprobiotics, although they are inactive or not alive. This experiment once again proved that while using a nutraceutical which has inhibitory effect on probiotics, paraprobiotics with their immunomodulins is the best and preferred choice to use to enhance its therapeutic effect. In this example also, it was proven that the amount of turmeric can be reduced by 33% with the inclusion of paraprobiotics along with their postbiotics, yet with a greater efficiency to control the ailments.

TABLE 6

Nutraceutical supplement composition(s) of single herb turmeric
with or without inclusion of probiotics, with or without inclusion of paraprobiotics
(along with their postbiotics), or without inclusion of postbiotics, and their effect on
general health, reduction of paindue to arthritis, and reduction of depression.
CODING: (−) Bad*, (+) slight improvement, (++) better, (+++) excellent

|  | Symptoms after 1 month administration | | | Symptoms after 2 months administration | | |
| --- | --- | --- | --- | --- | --- | --- |
| Variables and quantity/capsule | General Health Improvement | Reduction of pain | Reduction of anxiety & depression | General Health Improvement | Reduction of pain | Reduction of anxiety & depression |
| Turmeric - 750 mg | − | + | + | + | + | + |
| Turmeric - 500 mg + **Probiotics - 250 mg | +++ | + | + | ++ | +++ | ++ |

TABLE 6-continued

Nutraceutical supplement composition(s) of single herb turmeric
with or without inclusion of probiotics, with or without inclusion of paraprobiotics
(along with their postbiotics), or without inclusion of postbiotics, and their effect on
general health, reduction of paindue to arthritis, and reduction of depression.
CODING: (−) Bad*, (+) slight improvement, (++) better, (+++) excellent

| | Symptoms after 1 month administration | | | Symptoms after 2 months administration | | |
|---|---|---|---|---|---|---|
| Variables and quantity/capsule | General Health Improvement | Reduction of pain | Reduction of anxiety & depression | General Health Improvement | Reduction of pain | Reduction of anxiety & depression |
| Probiotics only - 750 mg | − | + | − | + | + | ++ |
| Turmeric - 500 mg + ***Paraprobiotics 250 mg | +++ | ++ | + | +++ | +++ | +++ |
| Paraprobioticsonly - 750 mg | + | + | + | + | + | + |
| Turmeric - 500 mg + 250 mg Postbiotics**** | + | + | + | ++ | ++ | ++ |
| Postbiotics only - 750 mg | − | − | − | + | − | − |

*Symptoms before administration:General health (−), pain (−), and depression (−).
**Probiotics used in equal proportion of 33:33:33: Live *Lactobacillus bulgaricus*, *Lactobacillus acidophilus*, and *Lactobacillus helveticus*, along with their growth end products.
***Paraprobiotics used in equal proportion of 33:33:33: Inactivated *Lactobacillus bulgaricus*, *Lactobacillus acidophilus* and *Lactobacillus helveticus* along with their growth end products.
****Postbiotics are growth end products of the above listed probiotics, without any live or inactivated paraprobiotics bacteria.

Example 6—A dietary supplement is formulated using multiple herbs, ashwagandha (30%)—basil (30%)—turmeric (27%)—neem (13%) and is named as STRATOGEN. The effects of using specific probiotics, paraprobiotics, and postbiotics along with STRATOGEN to increase the efficiency of STRATOGEN to improve the general health, sleep, and stamina had been studied by undertaking clinical trials. The STRATOGEN by itself served as a positive control. The probiotics, paraprobiotics, and postbiotics themselves served as negative controls in the study. The participants were asked to take two capsules per day, continuously for a period of two months only. The physicians were asked to examine the patients at monthly intervals and code the data.

The results of this study using seven variables including the STRATOGEN (multiple herbs only) are presented in Table 7. The results proved that STRATOGEN with live probiotics, STRATOGEN with inactive paraprobiotics, and STRATOGEN with postbiotics fared significantly better than STRATOGEN by itself, indicating that there is definitely synergy between multiple herbs and probiotics, paraprobiotics, and postbiotics to enhance the efficiency of the dietary supplement STRATOGEN. The negative controls although have some effect, they were inferior to STRATOGEN itself in terms of improving sleep pattern. All in all, this experiment proved beyond doubt that live probiotics can be replaced by inactive paraprobiotics along with postbiotics to improve the efficiency of dietary supplements, although paraprobiotics were slightly more efficient than only postbiotics. In this example although the probiotics and paraprobiotics both exhibited improved efficiency, the preferred ingredient is the postbiotics with immunomodulins, because of the inhibitory effect of neem on the probiotics. Thus, in a long hold the paraprobiotics along with their postbiotics are the best choice to replace the live probiotics, as per the preference or demand by some sectors of the medical communities with regard to specific objection on using probiotics in combination with the dietary or nutraceutical preparations.

TABLE 7

Dietary supplement STRATOGEN (multiple mixed herbs:
ashwagandha - basil - turmeric - neem), with or without inclusion of probiotics,
with or without inclusion of paraprobiotics (along with their postbiotics), or with
or without inclusion of Postbiotics on improving general health, improve sleep
and assisting improvement of stamina. **
CODING: (−) Bad*, *(+) - slight improvement, (++) - better improvement,
(+++) - excellent improvement

| | Symptoms after 1 month administration | | | Symptoms after 2 months administration | | |
|---|---|---|---|---|---|---|
| Variables and quantity/capsule | General Health | Improving sleep | Improving Stamina | General Health | Improving sleep | Improving stamina |
| STRATOGEN - 750 mg (without Probiotics) | + | + | + | ++ | + | + |

TABLE 7-continued

Dietary supplement STRATOGEN (multiple mixed herbs: ashwagandha - basil - turmeric - neem), with or without inclusion of probiotics, with or without inclusion of paraprobiotics (along with their postbiotics), or with or without inclusion of Postbiotics on improving general health, improve sleep and assisting improvement of stamina. **
CODING: (−) Bad*, *(+) - slight improvement, (++) - better improvement, (+++) - excellent improvement

| Variables and quantity/capsule | Symptoms after 1 month administration | | | Symptoms after 2 months administration | | |
| --- | --- | --- | --- | --- | --- | --- |
| | General Health | Improving sleep | Improving Stamina | General Health | Improving sleep | Improving stamina |
| STRATOGEN - 500 mg + ***Probiotics - 250 mg | ++ | ++ | ++ | +++ | ++ | ++ |
| Probiotics only - 750 mg | + | − | − | + | − | + |
| STRATOGEN - 500 mg + Paraprobiotics - 250 mg | ++ | ++ | ++ | +++ | ++ | ++ |
| ****Paraprobiotics only - 750 mg | + | − | − | + | + | + |
| STRATOGEN - 500 mg + 250 mg Postbiotics***** | + | ++ | + | ++ | ++ | + |
| Postbiotics only - 750 mg | + | − | − | + | − | + |

*STRATOGEN: Is an herbal combination of 30% ashwagandha, 30% basil, 27% turmeric and 13% neem.
** Symptoms before administration: General health (−), pain (−), and stamina (−).
***Probiotics used: Live *Streptococcus thermophilus* (25%), *Lactobacillus acidophilus* (25%), *Bacillus coagulans* (25%), and *Propionibacterium shermanii* (25%), along with their growth end products.
****Paraprobiotics used: Inactivated *Streptococcus thermophilus* (25%), *Lactobacillus acidophilus* (25%), *Bacillus coagulans* (25%), and *Propionibacterium shermanii* (25%), along with their growth end products.
*****Postbiotics are growth end products of the above listed probiotics, without any live or inactivated paraprobiotic bacteria.

Example 7—Few commercial herbal formulations or homeopathic formulations or supplements with different compositions and functions were purchased in the finished form to blend with the paraprobiotics or probiotics to check for the improved efficacy of the supplements, if any, in accordance with this invention. One such popular commercial herbal formulations is named SHA1 PLUS, an Ayurvedic herbal tonic which was intended for a healthy immune system, manufactured, and marketed by BVG Life Sciences limited, Pune, India. It was evaluated by including probiotics or paraprobiotics to check for improved efficiency, specifically to prevent or relieve symptoms of COVID-19 infection, although it was principally recommended to improve overall health, including cardiac functions.

The SHA1 PLUS had the following herbal Ayurvedic ingredients in every 10 ml: Sweet orange (*Citrus sinensis*), Eucalyptus (*Eucalyptus globulus*), Coriander (*Coriandrum sativum*), Tea (*Camellia sinensis*), Lavender (*Lavandula* sp.), Rosemary (*Rosmarinus officinalis*), Thyme (*Carum copticum*) each 0.05%; Oregano (*Origanum vulgare*), Bergamot (*Citrus bergamia*) each 0.15%; Spearmint (*Mentha arvensis*), Clove (*Syzygium aromaticum*), Peppermint (*Mentha piperata*), Cinnamon (*Cinnamomum verum*), Neem (*Azadirachta indica*), Lemon grass (*Cymbopogon citrus*), Blackseed (*Nigella sativa*) 0.10%; Coconut (*Coccus nucifera*) 2.1%; Corn (*Zea mays*), Sugar cane (*Saccharum officinarum*) each 1.5%; Excipients 1.0%; water Q-S. It is purchased as a liquid preparation of 200 ml in glass bottles.

As part of the experiment, probiotics used in SHA1 PLUS are as follows: *Lactobacillus acidophilus* (25%), *Streptococcus thermophilus* (25%), and *Lactococcus lactis* subsp. *lactis* (25%), and *Propionibacterium freudenreichii* (25%). For every 200 ml of the SHA1 PLUS formula, 0.5 ml of the liquid probiotic preparation or 0.5 ml of the liquid paraprobiotic preparation were added separately, to study the effect of live probiotics vs. paraprobiotics along with their immunomodulins, in enhancing the efficacy of SHA1 PLUS to improve or assist the general health.

SHA1 PLUS by itself was used as control. Dosage recommended by the manufacturer for SHA1 PLUS was 5 ml per day (1 teaspoon) for children and 5 to 10 ml (1-2 teaspoons) twice a day for adults. In other words, the daily dose recommended for adults is 10 to 12 ml per day. The SHA1 PLUS probiotics (0.5 ml liquid probiotic/200 ml) and SHA1 PLUS paraprobiotic (0.5 ml liquid paraprobiotic along with postbiotics/200 ml) were evaluated for the improvement of efficiency of SHA1 PLUS. SHA1 PLUS by itself was very effective as per the instructions of the manufacturer. This supplement was evaluated to see if it can assist in preventing COVID-19 vs. to cure COVID-19. The results of the trial proved that inclusion in SHA1 PLUS of probiotics slightly improved the efficacy of SHA1 PLUS and the results are presented in Table 8. However, paraprobiotics along with postbiotics inclusion significantly improved the efficacy of SHA1 PLUS on the basis of symptoms pertaining to the overall general health improvement, and prevention or treatment of COVID-19 infection due to SARS-COV-2 coronavirus. The people who took SHA1 PLUS along with paraprobiotics plus postbiotics under their physician's watch commented that it worked both as preventative and as a curative on COVID-19 infections. Although it is intended to improve immunity, it was discovered serendipitously as miraculous supplement to prevent or cure COVID-19 disease or for that matter any other viral infections, including but not limited to seasonal flu due to influenza virus.

The inclusion of paraprobiotics specifically proved to be effective in preventing COVID-19 infection, proven by negative RT-PCR test of the subject. In addition, the COVID-19 positive patients also reported that their recovery was very good; as evidenced by their improved symptoms as well as breathing pattern. In addition to negative RT-PCR test and oxygen levels (95 to 100), these preparations were very effective even when used at half the dose recommended by the manufacturer. Although these experiments were conducted on a limited number of people, the results clearly indicated that inclusion of probiotics or paraprobiotics improved the efficacy of this herbal Ayurvedic preparation, SHA1 PLUS. Since probiotics do not survive in liquids, it is not a good practice to use live organisms in liquid, and thus it is highly preferable to use paraprobiotics. Apparently, the improvement of immune system due to paraprobiotics addition with the Ayurvedic preparation was very significant proving the merit of the current invention. The invention is novel in that the paraprobiotics along with their postbiotics were far superior to the probiotics only. Apparently the probiotics were inhibited by some of the ingredients in the formula. Besides it was proven beyond doubt that the paraprobiotics along with their immunomodulins are the best choice to use in the liquid preparation, to enhance the therapeutic effect of the drug or the supplement.

under the tongue every 15 minutes for 1 hour, and then dissolve 5 pellets under the tongue 3 times a day until symptoms are relieved." The experimental test variables (probiotics, paraprobiotics, postbiotics), in liquid form were applied individually at 0.1 gm or 0.1 ml on to the pellets as fine spray. The test variables were also administered following the same directions and dosage as the unfortified homeopathic pallets. The composition of variables and the clinical test results are presented in Table 9.

The results proved that the symptoms of hay fever (allergic Rhinitis) were reduced by HISTAMINUM 30 C. However, according to other subjects, the symptoms of hay fever were significantly reduced at a much faster pace with the variable HISTAMINUM 30C plus the paraprobiotic composed of *Lactobacillus acidophilus, Lactobacillus rhamnosus, Streptococcus thermophilus* and *Lactococcus lactis* var *lactis* (in equal proportions). The paraprobiotics along with postbiotics addition was far superior to probiotics. Similar observations were made with the use of the variables on reducing the symptoms of hives. The active ingredient in HISTAMINUM 30C, is histaminum hydrochloride 30C HPUS (0.443 mg) per pellet, and the inactive ingredients are lactose and sucrose. The results proved that the efficacy of the homeopathic medicines can be significantly improved by fortifying them with paraprobiotics or postbiotics or probi-

TABLE 8A

COVID-19 Symptoms before treatment
CODING: (−) - Bad, (+) - Slight improvement, (++) - Better improvement, (+++) - Excellent

| Variable | Shortness of breath | Fever | Oxygen levels | RT-PCR test | General dullness | General stamina |
|---|---|---|---|---|---|---|
| SHAT PLUS | − | 101-103 F. | 85-90 | + | − | − |
| SHAT PLUS + Probiotics* | − | 101-103 F. | 85-90 | + | − | − |
| SHAT PLUS + Paraprobiotics** | − | 100-103 F. | 85-90 | + | − | − |

TABLE 8B

COVID-19 symptoms after treatment

| Variable | Shortness of breath | Fever | Oxygen levels | RT-PCR test | General dullness | Overall stamina | Side effects |
|---|---|---|---|---|---|---|---|
| SHAT PLUS | + | 100-102 | 92-94 | +(25%) & −(75%) | + | ++ | ***ND |
| SHAT PLUS + probiotics* | ++ | 98-100 | 94-96 | − | ++ | ++ | ND |
| SHAT PLUS + Paraprobiotics** | +++ | 97-99 | 98-99 | − | +++ | +++ | ND |

*Probiotic used: Live *Lactobacillus acidophilus* (25%), *Streptococcus thermophilus* (25%), *Lactococcus lactis subsp. lactis* (25%), and *Propionibacterium freudenreichii* (25%), along with their growth end products (immunomodulins or postbiotics).
**Paraprobiotics used: Inactivated *Lactobacillus acidophilus* (25%), *Streptococcus thermophilus* (25%), *Lactococcus lactis subsp. lactis* (25%), and *Propionibacterium freudenreichii* (25%), along with their growth end products (immunomodulins or postbiotics).
***ND - None detected.

Example 8—A commercially available HISTAMINUM 30C, an allergy relief homeopathic preparation made in France, but distributed by Boirun USA, was evaluated to improve its efficiency with inclusion of probiotics, paraprobiotics, and postbiotics individually, using HISTAMINUM 30C as control. The manufacturer's directions regarding dosage and frequency of using homeopathic medicament is as follows: "At the onset of symptoms, dissolve 5 pellets otics. Thus, to obviate the objection of using live probiotics by some physicians and patients, inactive paraprobiotics or postbiotics can be used safely to enhance the therapeutic effects of the homeopathic medicines, if the homeopathic pharmacopoeia allows such fortification. The results of this experiment clearly proved that use of paraprobiotic along with their immunomodulins exhibited far superior results to improve the efficacy of the homeopathic drugs, in comparison to live probiotics.

TABLE 9

The effect of HISTAMINUM 30C, a homeopathic medicine recommended for allergy relief (hay fever, hives), with or without inclusion of probiotics, paraprobiotics, and postbiotics individually.

| Test variables | Reduction of allergy symptoms after treatment | Frequency of recurrence of allergy symptoms after treatment | Side effects during treatment |
|---|---|---|---|
| HISTAMINUM 30C by itself | + | − | ND***** |
| HISTAMINUM 30C plus probiotics** | ++ | + | ND |
| HISTAMINUM 30C plus Paraprobiotics*** | ++ | + | ND |
| HISTAMINUM 30C plus postbiotics**** | + | − | ND |

Code: (−) bad*; (+) slight improvement; (++) Better; (+++) Excellent

*Symptoms before treatment: Severe allergy symptoms.

**Probiotics used in equal proportion of: Live *Lactobacillus acidophilus*, *Lactobacillus rhamnosus*, *Streptococcus thermophilus* and *Lactococcus lactis* var *lactis*, along with their growth end products.

***Paraprobiotics used in equal proportion of: Inactive *Lactobacillus acidophilus*, *Lactobacillus rhamnosus*, *Streptococcus thermophilus* and *Lactococcus lactis* var *lactis*, along with their growth end products.

****Postbiotics are the growth end products of the probiotics, without any live or inactive paraprobiotic bacteria.

*****ND-none detected.

Example 9—A commercially available homeopathic medicine made in France but distributed by Boiron Corp in USA, to reduce or treat hemorrhoids was fortified with probiotics or paraprobiotics or postbiotics to check if the efficiency of the homeopathic medicine can be improved. According to the directions of the distributor, Boiron, the commercial prep HEMCALM was supposed to be taken 2 tablets every two hours up to 6 times a day. The probiotics using the strains of *Bifidobacterium bifidus, Pediococcus acidilactici, Lactobacillus acidophilus*, and *Lactococcus lactis* var *lactis* ssp *diacetylactis* was applied through adsorption onto the tablet at a final concentration 0.1 gram per tablet, which served as a positive control. Similarly, the paraprobiotics and postbiotics made using the same probiotic composition was applied onto the HEMCALM tablets individually, which served as negative controls. All of the 4 variables were tested using HEMCALM by itself as a control, to study their effect on reducing the hemorrhoid discomfort of burning, itching, pain, and discomfort of the anal tissue. The composition of the variables and the test results are presented in Table 10.

The active ingredients in each of the HEMCALM tablet are as follows. *Asculus hippocastanum* 6× HPUS (0.83 mg), *Nux vomica* 12× HPUS (0.83 mg)—Contains less than 10-13 mg Alkaloids. The inactive ingredients are Croscamellose sodium, Lactose and Magnesium stearate. The letter HPUS indicates that the ingredients are officially monographed in the homeopathic pharmacopoeia of the United States.

The results presented in Table 10, indicate that the symptoms of the hemorrhoids were significantly reduced when HEMCALM homeopathic tablets were fortified with both the probiotics, paraprobiotics, and postbiotics individually, in comparison to the control HEMCALM. Although HEMCALM did reduce hemorrhoids symptoms, the effect was much more pronounced with fortification of paraprobiotics along with postbiotics and probiotics, followed by postbiotics. The test was conducted using only 4 individuals, and yet the results proved that probiotics or paraprobiotics or postbiotics can be incorporated with the homeopathic medications, to improve their effect significantly. However, the best preference is the use of paraprobiotics along with their postbiotics, considering the length of storage as well as the condition of the storage. Thus, even in the homeopathic medicines, the objection of using live probiotics can be obviated by replacing probiotics with paraprobiotics along with their postbiotics, with an improved performance.

It once again proves the novelty of the current invention. Surprisingly, even the postbiotics themselves infused into homeopathic medicament had the greatest effect in reducing the symptoms of hemorrhoids, as well as probiotics and paraprobiotics. Overall, this clinical trial significantly proved the superior efficiency of using paraprobiotics along with their postbiotics to replace the live probiotics even in the homeopathic medicines. It has been proven through our earlier experiments, through clinical trials in this investigation that paraprobiotics along with the postbiotics exhibited synergy in enhancing the therapeutic effect of supplements or drugs. Going forward in the additional examples 10 through 22, the term paraprobiotic denotes the combination of paraprobiotics along with their postbiotics or soluble growth end products or immunomodulins.

TABLE 10

The effect of HEMCALM, a homeopathic medicine to relieve symptoms of hemorrhoids, with or without inclusion of probiotics, paraprobiotics and postbiotics individually.

| Test variables | Reduction of hemorrhoids symptoms after treatment | Frequency of recurrence of hemorrhoids symptoms after treatment | Side effects during treatment |
|---|---|---|---|
| HEMCALM by itself | ++ | − | ND***** |
| HEMCALM plus probiotics** | +++ | ++ | ND |
| HEMCALM plus Paraprobiotics*** | +++ | ++ | ND |
| HEMCALM plus postbiotics**** | +++ | + | ND |

Code: (−) bad*; (+) slight improvement; (++) Better; (+++) Excellent
*Symptoms before treatment: Severe burning and itching.
**Probiotics used in equal proportion of: Live *Bifidobacterium bifidus*, *Pediococcus acidolactici*, *Lactobacillus acidophilus*, and *Lactococcus lactis* var *lactis* ssp *diacetylactis*, along with their growth end products.
***Paraprobiotics used in equal proportion of: Inactive *Bifidobacterium bifidus*, *Pediococcus acidolactici*, *Lactobacillus acidophilus*, and *Lactococcus lactis* var *lactis* ssp *diacetylactis*, along with their growth end products.
****Postbiotics are growth end products of the above listed probiotics, without any live or inactive paraprobiotic bacteria.
*****ND-None detected.

Example 10—An herbal and probiotic drug formulation as outlined in U.S. Pat. No. 6,080,401 was prepared as control and it is designated as MEMORY MAX. The same formula where probiotics were replaced by paraprobiotics along with their postbiotics is designated as MEMORY MAX PLUS. Here after starting from example 10 through 22, the paraprobiotics includes postbiotics, even though the term paraprobiotic only is used to eliminate the repetition of words. The MEMORY MAX minus probiotic served as herbal control, and probiotics themselves were used as negative probiotic controls. Similarly, paraprobiotics only without any herbs, i.e., MEMORY MAX, minus herbs, served as positive paraprobiotic controls. The MEMORY MAX was prepared using the composition outlined in Table 11. It was capsulated using 475 mg/capsule. Wherever probiotics were only used, the amount of probiotic used was 435 mg/capsule. Memory Max minus probiotic (herbs only) was capsulated using 425 mg/capsule to serve as herbal control. Similarly, the MEMORY MAX PLUS (herbs+paraprobiotics) using the composition outlined in Table 11 (where probiotics were replaced by paraprobiotics) was dispensed into capsules at 475 mg/capsule. Wherever paraprobiotics were only used, they were dispensed at 435 mg/capsule.

The clinical studies were conducted using 4 people to check each variable (20 people were involved in total to check all 5 variables). The physicians were instructed to recommend 2 capsules/day on a daily basis for a period of two months. The physicians were asked to code the data, including the side effects. None of the participants were told anything about the compositional variables. The comparison here is to check if paraprobiotics and postbiotics can successfully replace probiotics in the drug formula, MEMORY MAX, in terms of speedy recovery as well as successful cure of the disease, without any side effects. The patients were inspected for the relief of the following symptoms: tension, loss of memory, and depression. The results of the clinical studies are presented in Tables 12A-C.

The results, presented in Tables 12A-C, proved that MEMORY MAX (herbs+probiotics) was superior to either herbs by themselves or probiotics by themselves, proving once again that the results outlined in U.S. Pat. No. 6,080,401 were correct and reproducible. The MEMORY MAX PLUS (herbs+paraprobiotics) exhibited similar clinical results to decrease tension, restore memory, and decrease depression. The results of the experiment distinctly proved through clinical trials that live probiotics can be safely replaced by inactive paraprobiotics to improve the efficacy of herbs to treat the neurological conditions, at a faster pace, without any side effects. Apparently the paraprobiotics not only enhance the effect of herbs but also improve the therapeutic effect by stimulating or enhancing the immunity through proper immunomodulation to assist the drug. Apparently, the probiotics do not have to be live (to obviate the objection on live probiotics) to induce synergistic therapeutic effect in combination with herbal drug to treat the neurological conditions, with equal efficiency without any side effects.

TABLE 11

Composition of MEMORY MAX Herbal and Probiotic or Paraprobiotic Ingredients

| | Botanical Name | quantity (mg) per capsule |
|---|---|---|
| Herbs | Tinospora | 25 |
| | Withania somnifera | 30 |
| | Glycyrrhiza glabra | 30 |
| | Convolvulus pluricaulis | 50 |
| | Nardostachys jatamansi | 25 |
| | Terminalia chebula | 25 |
| | Piper nigrum | 25 |
| | Cissampelos pareira | 25 |
| | Acorus calamus | 25 |
| | Moringa oleifera | 25 |
| | Bacopa monnieri | 75 |
| Non-Herbal | Bitumen | 75 |
| Probiotics Or Paraprobiotics | Lactobacillus acidophilus | 40 |
| | Lactobacillus acidophilus | 40 |

TABLE 12A

Symptoms before treatment

| Variable | Tension | Loss of Memory | Depression |
|---|---|---|---|
| MEMORY MAX (herbs & probiotics) | 4 | 3 | 4 |
| MEMORY MAX minus probiotic | 4 | 3 | 4 |
| Probiotic only (no herbs) | 4 | 3 | 4 |
| MEMORY MAX (herbs & Paraprobiotic) | 4 | 3 | 4 |
| Paraprobiotic (no herbs) | 4 | 3 | 4 |

CODING: 4-severe, 3-modest, 2-slight, 1-cured, No-none detected.

TABLE 12B

Symptoms after one month of treatment

| Variable | Tension | Loss of Memory | Depression | Adverse Side Effect |
|---|---|---|---|---|
| MEMORY MAX (berbs & probiotics) | 1 | 2 | 1 | ND |
| MEMORY MAX minus probiotic | 4 | 3 | 4 | ND |
| Probiotic only (no herbs) | 3 | 3 | 4 | ND |
| MEMORY MAX (herbs & Paraprobiotic) | 1 | 1 | 1 | ND |
| Paraprobiotic only (no herb) | 3 | 3 | 3 | ND |

TABLE 12C

Symptoms after two months of treatment

| Variable | Tension | Loss of Memory | Depression | Adverse Side Effect |
|---|---|---|---|---|
| MEMORY MAX (herbs & probiotics) | 1 | 1 | 1 | ND |
| MEMORY MAX minus Probiotic | 3 | 3 | 3 | ND |
| Probiotic only (no herbs) | 3 | 3 | 4 | ND |
| MEMORY MAX (herbs & Paraprobiotic) | 1 | 1 | 1 | ND |
| Paraprobiotic only (no herbs) | 2 | 3 | 3 | ND |

Example 11—The variables prepared are same as in Example 10, except the drug and the probiotics or paraprobiotics were different. This herbal drug mixed with probiotics as outlined in Table 13 was named as FLEXIMAC (U.S. Pat. No. 6,080,401) which is formulated to treat symptoms associated with arthritis. The paraprobiotics were prepared according to the procedures outlined earlier. For the sake of convenience, the herbs plus paraprobiotic preparation was termed FLEXIMAC PLUS. The FLEXIMAC and FLEXIMAC PLUS were capsulated individually using 440 mg/capsules. The individual probiotics and paraprobiotics and herbs were capsulated at 400 mg per capsule. All 5 different composition capsules were given to patients to study their effects in reducing joint stiffness, swelling and pain due to arthritis. Physicians running clinical trials were asked to prescribe 2 capsules/day. A total of 20 participants were involved in the clinical trial and each variable was given to 4 patients. The subjects were asked to keep track of the improvements and side effects for a period of two months and communicate judiciously with their physician.

The result of the clinical trial is presented in Table 14. The results clearly proved that live probiotics can be replaced with inactive paraprobiotics in the FLEXIMAC drug composition. The variables also proved that postbiotics (growth end products only) of probiotics or paraprobiotics also had slight effect on reducing swelling. However, in combination with the specific herbs, intended to cure arthritis, both the probiotics and postbiotics exhibited similar properties in terms of curing or reducing the arthritis symptoms, thus proving live probiotics can be safely replaced by their counterpart inactive paraprobiotics. The probiotics and paraprobiotics used in this experiment are *Lactobacillus acidophilus* and *Bacillus coagulans* in equal proportions. The applicant has also discovered that the non-herbal Ayurvedic Dashamoola Kwatha Churna can be replaced by bio-available calcium with other major and minor minerals of milk origin, since some of the Ayurvedic Churnas have been criticized for having toxic metallic components such as arsenic, lead etc. In addition, the formulations given to the pet dogs and cats significantly improved the arthritic symptoms. However, the dosage was adjusted according to their body weight. It is proven that paraprobiotics can replace live probiotics in the drugs, to enhance their therapeutic effect, without any side effects.

TABLE 13

FLEXIMAC, Composition of FLEXIMAC, Herbal, Probiotic or Paraprobiotic ingredients

| | Botanical/Scientific Name | Quantity (mg) per capsule |
|---|---|---|
| Herbs | Commiphora mukul | 100 |
| | Zingiber officinale | 25 |
| | Curcuma zedoaria | 25 |
| | Ricinus communis | 50 |
| | Boerhaavia diffusa | 50 |
| | Pluchea ianceolata | 75 |
| | Strychnos nux vomica | 25 |
| Non-Herbal | Dashamoola Kwatha Churna | 50 |
| Probiotics | Lactobacillus acidophilus | 20 |
| | Bacillus coagulans | 20 |
| Or | Lactobacillus acidophilus | 20 |
| Paraprobiotics | Bacillus coagulans | 20 |

TABLE 14A

Symptoms before treatment

| Variable | Stiffness | Swelling | Pain |
|---|---|---|---|
| FLEXIMAC (herbs & Probiotic) | 3 | 2 | 3 |
| FLEXIMAC minus Probiotic (herbs only) | 3 | 2 | 3 |
| Probiotic only (no herbs) | 3 | 2 | 3 |
| FLEXIMAC (herbs & Paraprobiotic) | 3 | 2 | 3 |
| Paraprobiotic only | 3 | 2 | 3 |

CODING: 4-severe, 3-modest, 2-slighy, 1-cured, ND-none detected

TABLE 14B

Symptoms after one month treatment

| Variable | Stiffness | Swelling | Pain | Adverse Side Effects |
|---|---|---|---|---|
| FLEXIMAC (herbal & Probiotic) | 2 | 1 | 1 | ND |
| FLEXIMAC minus Probiotic (herbs only) | 3 | 2 | 3 | ND |
| Probiotic only (no herbs) | 3 | 2 | 3 | ND |
| FLEXIMAC (herbs & Paraprobiotic) | 2 | 1 | 1 | ND |
| Paraprobiotic only | 3 | 3 | 3 | ND |

TABLE 14C

Symptoms after two months treatment

| Variable | Stiffness | Swelling | Pain | Adverse Side Effects |
|---|---|---|---|---|
| FLEXIMAC (herbal & Probiotic) | 1 | 1 | 1 | ND |
| FLEXIMAC minus Probiotic (herbs only) | 3 | 2 | 3 | ND |
| Probiotic only (no herbs) | 3 | 2 | 3 | ND |
| FLEXIMAC (herbs & Paraprobiotic) | 1 | 1 | 1 | ND |
| Paraprobiotic only | 3 | 2 | 3 | ND |

Example 12—An herbal remedy was formulated as outlined in U.S. Pat. No. 6,080,401 using the herbs and probiotic *Bacillus coagulans*. This formula was referred to as LIVAD, which is intended to treat symptoms associated with liver dysfunction. The composition of LIVAD is presented in Table 15. A similar herbal formula with the inclusion of inactive paraprobiotic of *Bacillus coagulans* was referred to as LIVAD PLUS. Both the preparations were capsulated using 665 mg/capsule. The probiotics along with their postbiotics, paraprobiotics along with their postbiotics, and herbs only, are individually capsulated using 625 mg/capsule. All five variables were given to 5 sets of patients, with each set involving 4 people. They were asked to take 2 capsules/day for two months and were asked to report the results to their physicians. The physicians were asked to code the data carefully, including any or all side effects associated with each variable. The results of these clinical trials are presented in Table 16.

The results clearly proved that the LIVAD (herbs with live probiotic) and LIVAD PLUS (herbs+inactive paraprobiotics) had exhibited similar properties to reduce the hepatitis symptoms. Apparently the paraprobiotics also exhibited synergistic effects, like their counterpart live probiotics, to enhance the therapeutic effect of the herbal drug to treat the symptoms of liver dysfunction at a faster pace, without any side effects.

TABLE 15

Composition of LIVAD, Herbal, Probiotic or Paraprobiotic ingredients

| | Botanical/ Scientific Name | quantity (mg) per capsule |
|---|---|---|
| Herbs | Phyllanthus urinaria | 75 |
| | Swertia chirata | 75 |
| | Boerhaavia diffusa | 50 |
| | Curcuma longa | 50 |
| | Aloe barbedensis | 25 |
| | Tephrosia purpurea | 50 |
| | Tinospora cordifolia | 25 |
| | Eclipta alba | 50 |
| | Terminalia chebula | 25 |
| | Terminalia belerica | 25 |
| | Phyllanthus Emblica | 25 |
| Non-Herbal Ayurvedics | Shringa Bhasma (Sanskrit Name) | 50 |
| Non-Herbal Ayurvedics | Mandur Bhasma (Sanskrit Name) | 50 |
| Non-Herbal Ayurvedics | Kaseesa Bhasma (Sanskrit Name) | 50 |
| Probiotics Or Paraprobiotics | Lactobacillus sporogenes | 40 |
| | Lactobacillus sporogenes | 40 |

TABLE 16

Effect of LIVAD, LIVAD minus Probiotic, Probiotic only, LIVAD with Paraprobiotic (in place of probiotic) and Paraprobiotic only, on patients with clinical symptoms.

| | Symptoms Before Treatment | Symptoms After 1 Month of Treatment | | Symptoms After 2 Months of Treatment | |
|---|---|---|---|---|---|
| Variable | Typical Hepatitis Symptoms | Typical Hepatitis Symptoms | Adverse Side Effects | Typical Hepatitis Symptoms | Adverse Side Effects |
| LIVAD (herbs & Probiotics) | 4 | 1 | ND | 1 | ND |
| LIVAD minus Probiotic (herbs only) | 4 | 3 | ND | 2 | ND |
| Probiotic only | 4 | 3 | ND | 3 | ND |
| LIVAD Herbs & Probiotic | 4 | 1 | ND | 1 | ND |
| Parapbiotic | 4 | 2 | ND | 3 | ND |

CODING: 4-severe, 3-modest, 2-slighy, 1-cured, ND-none detected

Example 13—A combined drug of Ayurvedic herbs and probiotics, to treat the symptoms of anemia, was formulated using the composition outlined in U.S. Pat. No. 6,080,401. This preparation was referred to as HEMAC and the composition is presented in Table 17. The probiotics used in HEMAC are *Lactobacillus bulgaricus, Streptococcus thermophilus* and *Lactococcus lactis* var *lactis*. To check the effect of replacing above live probiotics with the inactive paraprobiotics on improving the drug efficiency, the drugs were prepared accordingly using the variables. The HEMAC formula where the probiotics were replaced by paraprobiotics was referred to as HEMAC PLUS, for identification purpose. Both the HEMAC and HEMAC PLUS were packed individually in capsules using 440 mg per capsule. Herbs only (without probiotics or paraprobiotics) were capsulated using 400 mg/per capsule, to serve as a negative control. The probiotics and paraprobiotics without any herbs were individually packed using 400 mg/capsule, also to serve as negative controls in the clinical trials. The probiotic and paraprobiotic (400 mg/capsule) were prepared separately using 200 mg of *Lactobacillus bulgaricus*, 100 mg of *Streptococcus thermophilus* and 100 mg *Lactococcus lactis* var *lactis* per capsule.

Once again 20 people were included in the clinical trials. They were divided in 5 groups, each group having 4 anemic patients, to test the formulas represented with 5 variables. They were asked to take 2 capsules/day for a period of two months and report the data (including any side effects) to their respective physicians. The physicians were asked to check the patients periodically for the relief of anemia symptoms, and code the data as accurately as possible. The results are presented in Table 18. The results revealed that both the HEMAC (herbs+plus live probiotic) and HEMAC PLUS (herbs+plus inactive probiotics) exhibited similar positive therapeutic effects both in terms of speed of recovery and not having any adverse side effects. This clinical trials distinctly proved that paraprobiotics also exhibited synergistic effect with drugs, like live probiotics, and thus they can serve as safe replacements, to override the objections raised on using live probiotics. In addition, even the paraprobiotic themselves have some therapeutic effect like their counter part live probiotics. Surprisingly the paraprobiotics along with their postbiotics by themselves (without any herbs) exhibited some improvement in curing anemia at the end of 2 months treatment period, signifying even dysbiosis was corrected by the paraprobiotics.

In addition, the applicant has discovered that Ayurvedic non-herbal Bhasmas can be safely replaced by bio-available calcium along with major and minor milk minerals in equal amount, since the use of Bhasmas had been criticized for having toxic metal contaminants. HEMAC and HEMAC PLUS also were tested on anemic dogs and cats using a dosage prorated according to their body weight. The results were favorable indicating that HEMACPLUS (herbs+paraprobiotics) was effective in treating anemic symptoms in household pets and thus they can be used safely in veterinary preparations and practice.

TABLE 17

Composition of HEMAC, Ayurvedic herbal and Non-herbal and Probiotic ingredients

|  | Botanical/Scientific Name | Quantity (mg) per capsule |
|---|---|---|
| Herbs | Hemidesmus indicus | 50 |
|  | Piper nigrum | 50 |
|  | Asparagus racemosus | 50 |
|  | Azadirachta indica | 75 |
| Non-Herbal Ayurvedics | Mandur Bhasma (Sanskrit Name) | 50 |
|  | Kaseesa Bhasma (Sanskrit Name) | 50 |
|  | Shringi Bhasma (Sanskrit Name) | 50 |
|  | Rasasindhur (Sanskrit Name) | 25 |
| Probiotics | Lactobacillus bulgaricus | 20 |
|  | Streptococcus thermophilus | 10 |
|  | Lactococcus lactis var lactic | 10 |
| Or Paraprobiotics | Lactobacillus bulgaricus | 20 |
|  | Streptococcus thermophilus | 10 |
|  | Lactococcus lactis var lactic | 10 |

TABLE 18

Effect of HEMAC, HEMAC minus Probiotics, Probiotic only, HEMAC with Paraprobiotics (in place of probiotics), and Paraprobiotics only, on patients with anemic clinical symptoms.

| No: Variable | Symptoms Before Treatment Anemic Symptoms | Symptoms After 1-Month of Treatment | | Symptoms After 2-Months of Treatment | |
|---|---|---|---|---|---|
| | | Anemic Symptoms | Adverse Side Effects | Anemic Symptoms | Adverse Side Effects |
| HEMAC (Herbs & Probiotics) | 3 | 2 | ND | 1 | ND |
| HEMAC minus Probiotics (Herbs only) | 3 | 3 | ND | 3 | ND |
| Probiotics (Herbs only) | 3 | 3 | ND | 3 | ND |
| Herbs & Paraprobiotics | 3 | 2 | ND |  | ND |
| Paraprobiotics Only | 3 | 3 | ND | 1 | ND |

CODING: 4-severe, 3-modest, 2-slighy, 1-cured, ND-none detected

Example 14—The herbal and probiotic blend product to treat the digestive disorders is named as DIGEST O MAX, whose composition is presented in Table 19. The selective probiotics were matched to improve the efficacy of the herbs to treat the symptoms of digestive disorders at a much faster pace with least side effects, according to the U.S. Pat. No. 6,080,401. Applicant's aim in this example is to see if live probiotics can be replaced by their inactivated counterpart probiotics with the same efficacy and without any side effects, to overcome the objection raised by some of the physicians and health professionals to pairing live probiotics with the drugs used to treat digestive disorders. The term DIGEST O MAX PLUS was given for the herbal composition outlined in Table 19, where the probiotics were replaced by using the same quantity of paraprobiotics. Both the DIGEST O MAX (herbs+probiotics) and DIGEST O MAX PLUS were packed individually using 540 mg per capsule. Herbs alone (positive control), probiotics alone, and paraprobiotics alone (negative controls) were packed individually using 500 mg per capsule. The microbial composition of live probiotics and inactive paraprobiotics used per capsule were as follows: *Penicillium roquefortii*-62.5 mg; *Penicillium camembertii*-62.5 mg; *Leuconostoc mesenteroides* ssp. *cremoris*-125.0 mg; *Enterococcus faecium*-62.5 mg; *Brevibacterium linens*-62.5 mg; *Saccharomyces boulardii*-62.5 mg.

The clinical studies were conducted on 5 different groups of individuals of each group having only 4 patients, who have digestive disorders. They were asked to take 2 capsules/day, for a period of 2 months on a continues basis. The physicians were asked to examine the patients and code the data including therapeutic improvements as well as any observable side effects. The results of the study are presented in Table 20 A-C. The results proved that DIGEST O MAX (herbs+probiotics) and DIGEST O MAX PLUS (herbs+probiotics) were equally effective to cure the symptoms of digestion, indicating the live probiotics can be replaced with paraprobiotics. The experiment revealed that the paraprobiotic does enhance the drug efficiency, without any side effects, proving that synergy does exist between herbs used and paraprobiotics, like probiotics as outlined in U.S. Pat. No. 6,080,401.

TABLE 19

Composition of DIGEST O MAX, Herbal, and Probiotic or Paraprobiotic ingredients

| | Botanical/Scientific Name | quantity (mg) per capsule |
|---|---|---|
| Herbs | Carica papaya | 75 |
| | Plumbago zeylanica | 75 |
| | Piper longum | 50 |
| | Piper nigrum | 50 |
| | Zingiber officinale | 50 |
| | Ferula foetida | 50 |
| | Aconitum heterophyllum | 25 |
| Non-Herbal | Saindhava Lavana (Sanskrit Name) | 25 |
| Ayurvedics | Sarjaksheera (Sanskrit Name) | 50 |
| | Yavakshara (Sanskrit Name) | 50 |
| Probiotics | Penicillium roquefortii | 5 |
| | Penicillium camembertii | 5 |
| | Leuconostoc mesenteroides ssp cremoris | 5 |
| | Streptococcus faecium | 5 |
| | Brevibacterium linens | 5 |
| | Saccharomyces cerevisiae | 5 |
| Or Paraprobiotic | Penicillium roquefortii | 5 |
| | Penicillium camembertii | 5 |
| | Leuconostoc mesenteroides ssp cremoris | 5 |
| | Streptococcus faecium | 5 |
| | Brevibacterium linens | 5 |
| | Saccharomyces cerevisiae | 5 |

TABLE 20 A

Symptoms before treatment

| Variable | Constipation | General Condition | Bowel Movement Regularity |
|---|---|---|---|
| DIGEST O MAX (herbs & Probiotics) | 4 | 3 | 4 |
| DIGEST O MAX minus Probiotic (herbs only) | 4 | 3 | 4 |
| Probiotics only | 4 | 3 | 4 |
| DIGEST O MAX (herbs & Paraprobiotics) | 4 | 3 | 4 |
| Paraprobiotics | 4 | 3 | 4 |

CODING: 4-severe, 3-modest, 2-slight, 1-cured, ND-none detected

TABLE 20 B

Symptoms after 1 month treatment

| Variable | Constipation | General Condition | Bowel Movement Regularity | Adverse Side Effects |
|---|---|---|---|---|
| DIGEST O MAX (herbs & Probiotic) | 1 | 1 | 1 | ND |
| DIGEST O MAX minus Probiotic (herbs only) | 2 | 2 | 2 | ND |
| Probiotic only (no herbs) | 3 | 2 | 3 | ND |
| DIGEST O MAX (herbs & Paraprobiotic) | 1 | 1 | 1 | ND |
| Paraprobiotic only | 3 | 2 | 3 | ND |

TABLE 20 C

Symptoms after 2 months treatment

| Variable | Constipation | General Condition | Bowel Movement Regularity | Adverse Side Effects |
|---|---|---|---|---|
| DIGEST O MAX (herbs & Probiotic) | 1 | 1 | 1 | ND |
| DIGEST O MAX minus Probiotic (herbs only) | 2 | 2 | 2 | ND |
| Probiotic only (no herbs) | 3 | 2 | 3 | ND |
| DIGEST O MAX (herbs & Paraprobiotic) | 1 | 1 | 1 | ND |
| Paraprobiotic only | 3 | 2 | 3 | ND |

Example 15—To treat hemorrhoids, pain, and rectal bleeding, an herbal formula with probiotic was developed and reported in U.S. Pat. No. 6,080,401. This formula was referred to as PILO-GUARD. To check the effect of PILO-GUARD with inclusion of inactive probiotics in place of probiotics to treat hemorrhoids, pain, and rectal bleeding without any side effects, a new formula was developed. This preparation was designated as PILO-GUARD PLUS and the composition of which is presented in Table 21. The probiotics and paraprobiotics included in the formulations were as follows: Bifidobacterium bifidus, Pediococcus acidilactici, Lactobacillus acidophilus, and Lactococcus lactis var lactis ssp diacetylactis. Both the PILO-GUARD (herbs+live probiotics) and PILO-GUARD (herbs+inactive paraprobiotics) were capsulated separately using 540 mg per capsule. Herbs only were packed at 500 mg per capsule to be used as positive control in the clinical trials. The live probiotics and inactive paraprobiotics were capsulated individually using the following amounts of live or inactive paraprobiotic bacteria: Bifidobacterium bifidus—125 mg; Pediococcus acidilactici—125 mg; Lactobacillus acidophilus—125 mg; Lactococcus lactis var lactis ssp diacetylactis—125 mg.

All five preparations, with each one with different variables, were given to 5 sets of patients (with each set having 4 patients). The patients were asked to take two capsules/day and monitor the symptoms and other side effects on a weekly basis. The patients were physically checked and monitored once a month for a period of two months. The results of the clinical trials are presented in Tables 22 A-C. The results indicate that the drug PILO-GUARD PLUS (with herbs and inactive paraprobiotics), performed slightly better even after one month treatment compared to PILO-GUARD (herbs+live probiotics). However, at the end of two months treatment, the performance was identical with both the preps, indicating that live probiotics can be replaced by inactive paraprobiotic, with excellent performance to treat hemorrhoids at a faster pace, without any side effects. It was also observed that paraprobiotics themselves exhibited better performance than the live probiotics to reduce hemorrhoids. Apparently paraprobiotics exert the effect primarily through immunomodulation and secondarily by maintaining the homeostasis and optimal composition of the gastrointestinal microbiota. This is the first investigation, where it is proven, that paraprobiotics can be mixed with specific drugs to enhance the drug efficiency to obviate the use of objected live probiotic inclusion. These preparations were proven effective even to reduce anal pruritus in household dogs and cats. This experiment proved beyond doubt that paraprobiotics can not only replace probiotics, but also exhibited improved efficiency to improve the therapeutic effect of the drug PILO-GUARD to reduce pruritus as well as hemorrhoids, both in humans as well as in animals.

TABLE 21

PILO-GUARD, Composition of PILO-GUARD, Herbal and Probiotic or Paraprobiotics ingredients

| Herbs | Botanical/Scientific Name | Quantity (mg) capsule |
|---|---|---|
| Herbs | Acacia catechu | 50 |
|  | Achyranthes aspera | 25 |
|  | Aloe barbadensis | 50 |
|  | Bauhinia variegata | 25 |
|  | Berberis aristana | 50 |
|  | Calotropis gigantea | 50 |
|  | Azadirachta indica | 50 |
|  | Plumbago zeylanica | 50 |
|  | Ricimis communis | 50 |
|  | Woodfordia fruticosa | 50 |
|  | Curcuma longa | 50 |
| Probiotics | Bifidobacterium bifidus | 10 |
|  | Pediococcus acidolactici | 10 |
|  | Lactobacillus acidophilus | 10 |
|  | Lactococcus lactis var lactis ssp diacetylactis | 10 |
| Or Paraprobiotics | Bifidobacterium bifidus | 10 |
|  | Pediococcus acidolactici | 10 |
|  | Lactobacillus acidophilus | 10 |
|  | Lactococcus lactis varlactis ssp diacetylactis | 10 |

TABLE 22 A

Symptoms before treatment

| Variable | Hemorrhoids | Bleeding | Pain |
|---|---|---|---|
| PILO-GUARD (herbs & probiotic) | 4 | 3 | 2 |
| PILO-GUARD minus Probiotic (herbs only) | 4 | 3 | 3 |
| Probiotic only (no herbs) | 4 | 3 | 3 |
| PILO-GUARD (herbs & Paraprobiotic) | 4 | 3 | 3 |
| Paraprobiotic only | 1 | 3 | 3 |

CODING: 4-severe, 3-modest, 2-slight, 1-cured, ND-none detected

TABLE 22 B

Symptoms After 1 Month

| Variable | Hemorrhoids | Bleeding | Pain | Adverse Side Effects |
|---|---|---|---|---|
| PILO-GUARD (herbs & probiotic) | 2 | 2 | 2 | ND |
| PILO-GUARD minus Probiotic (herbs only) | 4 | 3 | 3 | ND |
| Probiotic only (no herbs) | 3 | 2 | 2 | ND |
| PILO-GUARD (herbs & Paraprobiotic) | 2 | 1 | 2 | ND |
| Paraprobiotic only | 3 | 2 | 2 | ND |

TABLE 22 C

Symptoms After 2 Month Treatment

| Variable | Hemorrhoids | Bleeding | Pain | Adverse Side Effects |
|---|---|---|---|---|
| PILO-GUARD (herbs & probiotic) | 1 | 1 | 1 | ND |
| PILO-GUARD minus Probiotic (herbs only) | 3 | 2 | 2 | ND |
| Probiotic only (no herbs) | 3 | 2 | 2 | ND |
| PILO-GUARD (herbs & Paraprobiotic) | 1 | 1 | 1 | ND |
| Paraprobiotic only | 2 | 2 | 2 | ND |

Example 16—Probiotics were added to an herbal remedy designed to treat symptoms of diabetes. The composition was called GLUFAC and is presented in Table 23. The live probiotics used in this formula were same as the ones outlined in U.S. Pat. No. 6,080,401, which are as follows: *Propionibacterium shermanii, Lactobacillus casei*, and *Lactobacillus acidophilus*. The same probiotics were heat treated to inactivate them (Paraprobiotics) and they were used in the place of probiotics, in the GLUFAC formula to see if they have the same drug enhancing property as live probiotics to cure or control diabetes, with no side effects. The drug with paraprobiotics was referred to as GLUFAC PLUS. In this example GLUFAC (herbs+live probiotics) and GLUFAC PLUS (herbs+inactive paraprobiotics) were dispensed into capsules individually using 565 mg per capsule. As a positive control herbs only were capsulated using 525 mg per capsule. Similarly, as a negative control, probiotics and paraprobiotics were capsulated individually using 525 mg per capsule. The quantity of individual components of mixed probiotic or paraprobiotic bacteria were as follows: *Propionibacterium shermanii*—131.25 mg; *Lactobacillus casei*—131.25 mg; *Lactobacillus acidophilus*—262.50 mg. For running experimental clinical trials patients with similar symptoms were divided into 5 panels, each panel consisting of 4 people. The patients were asked to take 2 capsules per day for two months. They were also asked to exercise or walk for at least 30 minutes a day. In addition, they were asked to eat less or least amount of carbohydrate for a period of two months. The physicians were asked to take patient's blood glucose levels once month. The results are presented in Table 24. To eliminate presenting too many figures, the data is presented as reduction of typical diabetes symptoms. The coding of data is as follows: Severe (4)-fasting blood sugar level over 300 mg/dl; moderate (3)-fasting blood sugar levels between 190 to 250 mg/dl; slight (2)-fasting blood sugar levels between 90 to 120 mg/dl. The results are presented in Table 24. The results indicate that both the GLUFAC (Herbs+live probiotics) as well as GLUFAC PLUS (herbs+inactive paraprobiotics) have similar effect in reducing the blood sugar levels, indicating that live probiotics can be replaced with inactive paraprobiotic in the herbal drug designed to treat diabetes. Surprisingly, although it is a limited data, the paraprobiotics by themselves reduced blood sugar levels significantly. The only explanation that can be given, with regard to the effect of paraprobiotics only, on reducing blood sugar levels can be due to stimulation of the beneficial indigenous bacteria in the GI tract microbiota, which might have indirectly reduced the blood sugar. In this experiment it is proven that the paraprobiotics along with their postbiotics performed well to replace live probiotics, to satisfy the physicians who were objecting to the use of live probiotics.

TABLE 23

GLUFAC; Composition of GLUFAC, Herbal and Probiotic or Paraprobiotic Ingredients.

|  | Botanical/Scientific Name | Quantity (mg) in each capsule |
|---|---|---|
| Herbs | Aegle marmelos | 50 |
|  | Azadirachta indica | 50 |
|  | Commiphora mukul | 50 |
|  | Curcuma longa | 50 |
|  | Syzygium cumini | 50 |
|  | Allium sativum | 50 |
|  | Pterocarpus marsupium | 50 |
|  | Gymnema sylvestre | 25 |
|  | Trigonella foenum | 75 |
|  | Tenninalia chebula | 25 |
|  | Tenninalia belerica | 25 |
|  | Phyllanthus emblica | 25 |
| Probiotics | Propionibacterium shermanii | 10 |
|  | Lactobacillus casei | 10 |
|  | Lactobacillus acidophilus | 20 |
| Or | Propionibacterium shermanii | 10 |
| Paraprobiotics | Lactobacillus casei | 10 |
|  | Lactobacillus acidophilus | 20 |

TABLE 24

Effect of GLUFAC, GLUFAC minus Probiotic, Probiotic only, GLUFAC with Paraprobiotic (in place of probiotics) Paraprobiotic only, on patients with diabetes clinical symptoms.

| No: Variable | Symptoms before Treatment | Symptoms after 1-month Treatment | | Symptoms after 2-months Treatment | |
|---|---|---|---|---|---|
|  | Typical Diabetes Symptoms | Typical Diabetes Symptoms | Adverse Side Effects | Typical Diabetes Symptoms | Adverse Side Effects |
| GLUFAC (herbs & Probiotics) | 3 | 2 | ND | 1 | ND |
| Probiotics Only | 3 | 3 | ND | 3 | ND |
| GLUFAC minus Probiotics (herbs only) | 3 | 3 | ND | 3 | ND |
| GLUFAC (herbs & paraprobiotics) | 3 | 2 | ND |  | ND |
| Paraprobiotics Only | 3 | 3 | ND | 1 | ND |

CODING: 4-severe, 3-modest, 2-slight, 1-cured, ND-none detected

Example 17—LIBIDO-MAX is an herbal preparation with inclusion of selective probiotics to treat impotency. The composition of LIBIDO-MAX is presented in Table 25. The LIBIDO-MAX, where live probiotics were replaced by inactive paraprobiotics is termed as LIBIDO-MAX PLUS for identification purposes. Both the LIBIDO-MAX and LIBIDO-MAX PLUS were capsulated separately using 750 mg per capsule. The herbal fraction only served as positive control whereas probiotics and paraprobiotics individually served as negative controls. All these three preparations were capsulated using 710 mg per capsule. The probiotics and paraprobiotic compositions bad the following quantities of individual probiotic strains: Lactobacillus acidophilus—177.50 mg; Lactobacillus bulgaricus—177.50 mg; Lactobacillus casei—177.50 mg; and Bacillus coagulans—177.50 mg.

The male subjects were asked to take two capsules per day, two hours before going to bed. Since there were five variables, 20 people were selected and they were divided into 5 groups. None of the subjects knew the composition of the capsules, more like a blind study. The patients were personally counseled on a weekly basis, continuously for a period of two months. The results are totally surprising in that LIBIDO-MAX PLUS (herb+paraprobiotics) greatly improved the sex drive in comparison to LIBIDO-MAX (herbs+probiotic). Even the negative controls paraprobiotics by themselves also improved sex drive slightly better than probiotics. Apparently paraprobiotics have synergistic effect with the herbal drug to enhance its effect without any side effects. One explanation is that probiotics must have stimulated the specific indigenous beneficial micro-organism(s) to interact positively with the herbs in the GI tract. There is another possibility in that the paraprobiotics must have improved the overall composition and homeostasis of the gastrointestinal microbiota and microbiome. Net effect, the experiment proved that inactive paraprobiotics can safely replace the objectionable live probiotics, in the drug formula, to enhance the sex drive, without inducing any side effects. The results of these clinical trials are presented in Table 26.

TABLE 25

LIBIDO-MAX, Composition of LIBIDO-MAX. Herbal and or Paraprobiotic ingredients

| Herbs | Botanical/Scientific Name | Quantity (mg) in each Capsule |
|---|---|---|
| Herbs | Withania somnifera | 75 |
|  | Mucuna pruriens | 75 |
|  | Tribulus terrestris | 50 |
|  | Tenninalia arjuna | 25 |
|  | Astercantha longifolia | 50 |
|  | Anacyclus pyrethrum | 50 |
|  | Myristica fragans | 50 |
|  | Sida cardifolia | 50 |
|  | Crocus sativus | 10 |
| Probiotics | Lactobacillus acidophilus | 10 |
|  | Lactobacillus bulgaricus | 10 |
|  | Lactobacillus casei | 10 |
|  | Lactobacilius sporogenes | 10 |
| Or | Lactobacillus acidophilus | 10 |
| Paraprobiotics | Lactobacillus bulgaricus | 10 |
|  | Lactobacillus casei | 10 |
|  | Lactobacilius sporogenes | 10 |

TABLE 26

Effect of LIBIDO-MAX, LIBIDO-MAX minus Probiotics, Probiotics only, LIBIDO-MAX with Paraprobiotic, and Paraprobiotic only, on patients with clinical symptoms.

| No: Variable | Symptoms before Treatment | Symptoms after 1-month of Treatment | | Symptoms after 2-months of Treatment | |
|---|---|---|---|---|---|
|  | Sex Drive | Sex Drive | Side effects | Sex Drive | Side effects |
| LIBIDO-MAX (herbs & Probiotics) | 1 | 3 | ND | 3 | ND |
| LIBIDO-MAX minus Probiotics (herbs only) | 1 | 2 | ND | 2 | ND |
| Probiotics only | 1 | 1 | ND | 3 | ND |
| LIBIDO-MAX (herbs & Paraprobiotics) | 1 | 2 | ND | 4 | ND |
| Paraprobiotics | 1 | 2 | ND | 2 | ND |

CODING:
4-Best,
3-Average,
2-Could be better,
1-Unsatisfactory,
ND-none detected Example 18—It has already been established in U.S. Pat. No. 6,080,401 that allopathic drugs efficiency can be significantly improved, with no side effects, by combining specific live probiotics with a specific allopathic drug of choice. Our study is undertaken to evaluate the efficiency of paraprobiotics in the place of live probiotics to improve the efficiency of an allopathic drug. An allopathic medicine with inclusion of probiotic was called PROZYME, and its composition is presented in Table 27. The PROZYME formula where the live probiotics were replaced by paraprobiotics is referred to as PROZYME PLUS. Five different formulations were created to run the clinical trials. The paraprobiotics alone, and probiotics alone were capsulated and used as negative controls. The allopathic formulation without the inclusion of probiotics served as a positive control. All 5 formulas were tested on patients who had been suffering with dyspepsia or indigestion. All five variables were tested on 20 different people, who were divided into 5 panels, with each panel having four patients. The patients were asked to take 1 capsule in the morning and one capsule in the evening every day, for a period of two months. The physicians were asked to code the data, including the speed of recovery and the side effects.

The results of the clinical trials are presented in Tables 28 A-C. The results proved that PROZYME (allopathic medicine+live probiotics) and PROZYME PLUS (allopathic medicine+inactive paraprobiotics) exhibited similar results in terms of reducing an uncomfortable feeling of fullness and an uncomfortable feeling of gassiness. In this particular instance, the variable with paraprobiotic only (PROZYME PLUS) cured the symptoms of dyspepsia faster and slightly better than the variable with live probiotics only (PROZYME). All in all, to cure dyspepsia successfully, live probiotics can be safely replaced by paraprobiotics in combination with the specific allopathic drug. In this instance, surprisingly paraprobiotics along with their postbiotics performed better than live probiotics to enhance the effect of the herbal drug formulation.

TABLE 27

PROZYME; (Allopathic formulation); Composition of allopathic formula PROZYME with Probiotic or Paraprobiotic; (PROZYME) to reduce dyspepsia; allopathic and Probiotic or Paraprobiotic Ingredients

|   | Applicable or Scientific Name | (mg) in each capsule |
|---|---|---|
| Allopathics | Fungal Diastase | 25 |
|  | Papain | 35 |
|  | Simethicone | 50 |
|  | Activated Charcoal | 75 |
| Probiotics | *Lactobacillus acidophilus* | 40 |
|  | *Bifidobacterium bifidus* | 20 |
|  | *Streptococcus faecium* | 20 |
| Or Paraprobiotics | *Lactobacillus acidophilus* | 40 |
|  | *Bifidobacterium bifidus* | 20 |
|  | *Streptococcus faecium* | 20 |

TABLE 28A

Symptoms before treatment

| Variable | Uncomfortable Feeling of fullness | Uncomfortable feeling of gassiness |
|---|---|---|
| PROZYME (Allopathic & Probiotic) | 4 | 4 |
| PROZYME minus Probiotic | 4 | 4 |
| Probiotic only (no herbs) | 4 | 4 |
| PROZYME (allopathic Formula and Paraprobiotic) | 4 | 4 |
| Paraprobiotics | 4 | 4 |

CODING:
4-Severe,
3-Modest,
2-Slight,
1-Cured,
ND-none detected

TABLE 28B

Symptoms after 1 month treatment

| Variable | Uncomfortable Feeling of fullness | Uncomfortable feeling of gassiness | Adverse side effects |
|---|---|---|---|
| PROZYME (Allopathic & Probiotic) | 1 | 1 | ND |
| PROZYME minus Probiotic | 3 | 3 | ND |
| Probiotic only | 4 | 2 | ND |
| PROZYME (allopathic & Paraprobiotic) | 1 | 1 | ND |
| Paraprobiotic only | 3 | 3 | ND |

TABLE 28C

Symptoms after 2 months treatment

| Variable | Uncomfortable Feeling of fullness | Uncomfortable feeling of gassiness | Adverse side effects |
|---|---|---|---|
| PROZYME (Allopathic & Probiotic) | 1 | 1 | ND |
| PROZYME minus Probiotic | 2 | 3 | ND |
| Probiotic only | 4 | 1 | ND |
| PROZYME (allopathic & Paraprobiotic) | 1 | 1 | ND |
| Paraprobiotic only | 3 | 2 | ND |

Example 19—An allopathic medicine, popularly used to reduce hypertension, was combined with selective probiotics, to improve the efficacy of the allopathic medicine to reduce both the systolic and diastolic blood pressure readings at a much faster pace, without any side effects, in comparison to allopathic medicine by itself. The allopathic medicine with probiotics is referred to as HYPERFAC, and its composition is outlined in Table 29. The allopathic medicine with inactive paraprobiotics (in the place of live probiotics) is referred to as HYPERFAC PLUS. The allopathic formula without live probiotics and inactive paraprobiotics (separately) served as negative controls. The patients with hypertension were asked to take one capsule per day. All 5 different variables were tested separately on 5 different groups of people. The physicians were asked to take their blood pressure readings once a week, for up to two months period. The averages of both systolic and diastolic pressures were coded in Tables 30 A-C.

The results of the clinical trials proved that the HYPERFAC (allopathic medicine+live probiotics) reduced the hypertension better than the allopathic medicine by itself. Surprisingly HYPERFAC PLUSreduced diastolic pressure better than HYPERFAC itself. Both the live probiotics by themselves and inactive paraprobiotics by themselves had slight effect in reducing both the systolic and diastolic pressure in comparison to the readings at the beginning of the treatment. However, both the live probiotics, and inactive paraprobiotics did exhibit synergistic effect when combined and administered along with the specific allopathic drugs, at a slightly faster pace with no side effects, to reduce hypertension. The net result is that inactive paraprobiotics can replace the live probiotics, even in the allopathic formulations, to eliminate the objection by physicians to use live probiotics with drugs.

TABLE 29

Composition of Allopathic Formula HYPERFAC with Probiotic or Paraprobiotic to reduce Hypertension: Allopathic and Probiotic Ingredients

| Variable | Pharmaceutical/Scientific Name | Quantity (mg) in each capsule |
|---|---|---|
| Allopathic | Nifedipine | 10 |
| | Atenolol | 25 |
| Probiotics | Lactobacillus acidophilus | 100 |
| | Bifidobacterium bifidus | 100 |
| or Paraprobiotics | Lactobacillus acidophilus | 100 |
| | Bifidobacterium bifidus | 100 |

TABLE 30 A

Symptoms before treatment.

| Variable | Range of systolic pressure | Range of diastolic pressure |
|---|---|---|
| HYPERFAC (Pharmaceutical & Probiotic) | 142--162 | 92--102 |
| HYPERFAC minus Probiotic (Pharmaceutical only) | 138--157 | 88--99 |
| Probiotic only | 140--160 | 91--97 |
| HYPERFAC (Pharmaceutical & Paraprobiotics | 150--175 | 90--100 |
| Paraprobiotics only | 147--170 | 93--98 |

TABLE 30B

Symptoms after 1 month of treatment.

| Variable | Range of systolic pressure | Range of diastolic pressure | Adverse side effects |
|---|---|---|---|
| HYPERFAC (Pharmaceutical & Probiotic) | 125--136 | 80--88 | ND* |
| HYPERFAC minus Probiotic (Pharmaceutical only) | 128--155 | 85--95 | ND |
| Probiotic only | 135--148 | 84--96 | ND |
| HYPERFAC (Pharmaceutical & Paraprobiotics | 128--140 | 78--82 | ND |
| Paraprobiotics only | 132--142 | 82--98 | ND |

TABLE 30C

Symptoms after 1 month of treatment.

| Variable | Range of systolic pressure | Range of diastolic pressure | Adverse side effects |
|---|---|---|---|
| HYPERFAC (Pharmaceutical & Probiotic) | 128--132 | 82--84 | ND* |

TABLE 30C-continued

Symptoms after 1 month of treatment.

| Variable | Range of systolic pressure | Range of diastolic pressure | Adverse side effects |
|---|---|---|---|
| HYPERFAC minus Probiotic (Pharmaceutical only) | 122--155 | 87--95 | ND |
| Probiotic only | 131--142 | 85--92 | ND |
| HYPERFAC (Pharmaceutical & Paraprobiotics | 130--132 | 76--82 | ND |
| Paraprobiotics only | 133--145 | 84--88 | ND |

*ND-none detected

Example 20—A broad-spectrum antibiotic tetracycline is mixed with probiotics to treat infection symptoms relating to sore throat and fever, without any side effects. The preparation is termed as BACTOMAC, and the breakdown of the compositional ingredients are listed in Table 31. A similar formula where the live probiotics were replaced with inactive paraprobiotic is referred to as BACTOMAC PLUS. The antibiotic by itself is used as positive control. The probiotics and paraprobiotics separately are used as negative controls. All the five variables were tried on 5 different sets of patients with infections with fever. Each patient was asked to take 2 capsules in the morning and 1 capsule in the evening for a period of 4 days. The physicians were asked to code the data at the end of the fourth day, for experimental purpose only, although antibiotic treatment has to be continued for a full course.

The results at the end of $4^a$ day revealed that BACTOMAC PLUS (antibiotic+paraprobiotic) performed better than BACTOMAC (antibiotic+probiotic), specifically in terms of reduction of general dullness. The results are presented in Table 32. Apparently the paraprobiotics were able to improve the immune system through exerted immunomodulation and also stimulate the indigenous microbiota to override the side effects of the antibiotics. This is an excellent observation because physicians are reluctant to mix antibiotics with live probiotics, due to fear of developing antibiotic resistant probiotic mutants, which can pass the resistant genes to the pathogenic bacteria. This is a breakthrough in that the concentration or amount of antibiotic administered to patients can also be significantly reduced due to the established synergy of antibiotics with inactive paraprobiotics. Further experiments proved that the dosage of antibiotic can be reduced by 35 to 50%.

TABLE 31

Composition of Allopathic Formula (BACTOMAC) with Probiotic or with Paraprobiotic to reduce infection: Allopathic and Probiotic Ingredients

| | Pharmaceutical/ Scientific Name | Quantity (mg) in each capsule |
|---|---|---|
| Antibiotics | Tetracycline | 500 |
| Probiotics | Lactobacillus acidophilus | 15 |
| | Streptococcus thermophilus | 15 |
| | Lactobacillus lactis var lactis | 5 |
| | Lactobacillus lactis var cremoris | 5 |
| Or | Lactobacillus acidophilus | 15 |
| Paraprobiotics | Streptococcus thermophilus | 15 |
| | Lactobacillus lactis var lactis | 5 |
| | Lactobacillus lactis var cremoris | 5 |

TABLE 32

Effect of BACTOMAC, BACTOMAC and Probiotic, Probiotic only,
BACTOMAC_and Paraprobiotic, and Parabiotic only, on patients with clinical symptoms.
CODING: 4 = Severe, 3 = modest, 2 = Slight, 1 = Cured, ND = none detected

| | Symptoms before treatment | | | Symptoms after 4 days of treatment | | | |
|---|---|---|---|---|---|---|---|
| Varible | Sore throat | Fever | General dullness | Sore throat | Fever | General dullness | Adverse side effects |
| BACTOMAC (Antibiotic & Probiotic) | 4 | 3 | 3 | 1 | 1 | 3 | ND |
| BACTOMAC Antibiotic only (no Probiotic) | 4 | 3 | 3 | 1 | 1 | 3 | ND |
| Probiotic only (no Antibiotic) | 4 | 3 | 3 | 3 | 2 | 3 | ND |
| BACTOMAC (Antibiotic & Paraprobiotic) | 4 | 3 | 3 | 1 | 1 | 1 | ND |
| Paraprobiotic only | 4 | 3 | 3 | 3 | 2 | 3 | ND |

Example 21—An herbal diet preparation was mixed with probiotics as an aid to reduce obesity and cholesterol. The composition of the preparation is listed in Table 33. The above preparation is named as HERBO DIET. The HERBO DIET with the inclusion of inactive paraprobiotics in the place of live probiotics is referred to as HERBO DIET PLUS. HERBO DIET without any probiotics served as a negative control. Patients were asked to take all the above three formulas (independently) 20 grams in the morning and 20 grams in the evening, diluting with water. The probiotic and paraprobiotic fractions only packed separately in sachets in 4 gram quantities were given to patients to serve as negative controls. The clinical trial was conducted for a period of two months. As a diet protocol all the participants were asked to exercise a minimum of 30 minutes per day, were asked to restrict the total daily calorie intake not exceed 1300 calories, and preferably should be around 1000 calories. The meal should have more protein, a moderate amount of fat, and the least amount of carbohydrate, to arrive at 1000 calories. Each patient was asked to take one multivitamin and one multimineral tablet per day to maintain their daily vitamin and mineral balance.

All the 5 variable composition diet plans to lose weight were given to 5 people only with each person with one variable. The physicians were asked to physically check the patient's general condition, weight, and also collect the blood samples (to check for cholesterol) at monthly intervals for up to two months only. The results of these clinical trials are presented in Table 24.

The results clearly revealed that both the HERBO DIET (herbs+live probiotics) and HERBO DIET PLUS (herbs+ inactive paraprobiotics) have exhibited positive effect in lowering the weight and cholesterol at the end of second month, compared to the HERBO DIET without any probiotics or paraprobiotics indicating that paraprobiotics can replace live probiotics in diet formula to enhance the therapeutic effect of specific herbs (fennel and fenugreek). Also, the HERBO DIET and HERBO DIET PLUS did not induce any adverse side effects such as constipation and reduction of overall general health condition of the patients.

TABLE 33

HERBO DIET; Composition of HERBO DIET

| | Common Name | Applicable Latin or Scientific Name | Preferred quantity (%) |
|---|---|---|---|
| Major Herbs | Fennel | Foeniculum officinale | 45 |
| | Fenugreek | Trigonella foenum-graecum | 22.5 |
| Minor Non-Herbal Food Grade Ingredients | Calcium Carbonate | | 0.5 |
| | Magnesium Hydroxide | | 0.5 |
| | Magnesium Sulfate | | 0.25 |
| | Lecithin | | 2 |
| | Guar Gum | | 2 |
| | Pectin | | 2 |
| | Cellulose | | 21.25 |
| Probiotics | | Lactobacillus acidophilus | 1 |
| | | Bifidobacterium bifidus | 1 |
| | | Bacillus coagulans | 1 |
| | | Saccharomyces boulardi | 1 |
| Or Paraprobiotics | | Lactobacillus acidophilus | 1 |
| | | Bifidobacterium bifidus | 1 |
| | | Bacillus coagulans | 1 |
| | | Saccharomyces boulardi | 1 |

TABLE 34

Effect of HERBO DIET on weight and cholesterol level, with controlled diet and exercise.
CODING: ND - None detected.

| | Before Treatment | | | After 2 months Treatment | | | |
|---|---|---|---|---|---|---|---|
| Variable | Weight (lbs) | Cholesterol mg/decileter | General condition | Weight lbs | Cholesterol mg/deciliter | Adverse Side effects | General condition |
| HERBO DIET | 206 | 262 | Below Average | 182 | 164 | ND | Good |
| HERBO DIET without Probiotic | 201 | 263 | Below Average | 196 | 213 | Mild constipation | Below average |
| Probiotic Only | 211 | 271 | Below Average | 199 | 251 | Severe Constipation | below average |
| HERBO DIET with Paraprobiotics | 217 | 255 | Below Average | 175 | 170 | ND | Good |
| Paraprobiotics Only | 210 | 248 | Below Average | 195 | 245 | Mild Constipation | Below average |

Example 22—To treat gum bleeding, bad breath, and toothache a formula using herbs and probiotics, as outlined in U.S. Pat. No. 6,080,401, was named as SUPERB, and the composition is presented in Table 35. To check the effect of replacing live probiotics with inactive paraprobiotics, a new formula with inactive paraprobiotics was developed, which is named as SUPERB PLUS. The SUPERB without the addition of live probiotics or inactive paraprobiotics served as negative control. These three formulas were tested by three groups of patients having bad breath, gum bleeding, toothache, and other periodontal disorders, for a period of 2 months. They were asked to brush twice a day using 5 grams of powder per brush.

The results revealed that both SUPERB (herbs+live probiotic) and SUPERB PLUS (herbs+inactive paraprobiotics) have reduced the symptoms of periodontal disease at a faster pace than the SUPERB without any live probiotics or inactive paraprobiotics. The results are presented in Tables 36 A-C. It clearly proved that inactive probiotics have similar therapeutic effect as live probiotics, in combination with the herbal drug. Thus, the objection placed on using live probiotics by dentists can be obviated by replacing live probiotics with paraprobiotics, with equal efficiency to treat the bad breath, toothache, and gum bleeding at a much faster pace, without any side effects. I have also discovered that adding bio-available calcium at a level of 2% to the herb plus probiotic, prepared either as powder or toothpaste, functioned very well to strengthen the gums and improve the shine of the teeth.

TABLE 35

SUPERB (Tooth Powder); Composition of
SUPERB (herbs plus Probiotic or Paraprobiotic), Herbal
and Probiotic or Paraprobiotic ingredients

| | Applicable Name | Applicable % |
|---|---|---|
| Herbs | Khadira | 6.75 |
| | Shilajit | 6.74 |
| | Guggulu | 5.40 |
| | Arka | 8.10 |
| | Cinchona | 5.40 |
| | Eucalyptus | 9.45 |
| | Vidonga | 8.10 |
| | Karkata Shringi | 5.40 |
| | Beejasara | 5.40 |
| | Ardhraka | 8.20 |
| | Amlaki | 13.51 |
| | Scariva | 6.65 |
| Probiotics | Lactobacillus acidophilus | 4.05 |
| | Lactobacillus lactis var lactis ssp diacetylactis | 3.37 |
| | Propionibacterium shermanii | 3.37 |
| Or Paraprobiotics | Lactobacillus acidophilus | 4.05 |
| | Lactobacillus lactis var lactis ssp diacetylactis | 3.37 |
| | Propionibacterium shermanii | 3.37 |

TABLE 36 A

Symptoms before treatment

| Variable | Gum bleeding | Tooth ache | Bad breath |
|---|---|---|---|
| SUPERB (herbs & Probiotic) | 4 | 4 | 4 |
| SUPERB minus Probiotic (herbs only) | 4 | 4 | 4 |
| SUPERB (herbs & Paraprobiotic) | 4 | 4 | 4 |

CODING:
4 = Severe,
3 = Modest,
2 = Slight,
1 = Cured,
ND = None detected.

TABLE 36B

Symptoms after 1 month of treatment

| Variable | Gum bleeding | Tooth ache | Bad breath | Adverse side effects |
|---|---|---|---|---|
| SUPERB (herbs & Probiotic) | 3 | 2 | 2 | ND |
| SUPERB minus Probiotic (herbs only) | 3 | 2 | 2 | ND |
| SUPERB (herbs & Paraprobiotic) | 2 | 2 | 1 | ND |

TABLE 36C

| | Symptoms after 2 months of treatment | | | |
|---|---|---|---|---|
| Variable | Gum bleeding | Tooth ache | Bad breath | Adverse side effects |
| SUPERB (herbs & Probiotic) | 1 | 1 | 1 | ND |
| SUPERB minus Probiotic (herbs only) | 1 | 1 | 2 | ND |
| SUPERB (herbs & Paraprobiotic) | 1 | 1 | 1 | ND |

The foregoing is considered as illustrative only of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow:

The invention claimed is:

1. A dosage unit of a therapeutic composition for improving stamina in a human or an animal subject in need thereof, wherein the dosage unit comprises:
   a first preparation of a non-enhanced therapeutic agent, wherein the non-enhanced therapeutic agent comprises an effective dosage of turmeric; and
   a second preparation comprising a mixture of paraprobiotics of inactivated probiotics of *Streptococcus thermophilus, Lactobacillus acidophilus, Bacillus coagulans*, and *Propionibacterium shermanii* and postbiotic growth end products or immunomodulins of said probiotics, wherein the mixture is present in a quantity sufficient to enhance the stamina-improving effect of the dosage unit,
   wherein the dosage unit does not comprise live probiotics and wherein the mixture in the second preparation enhances the stamina-improving effect of the dosage unit.

2. The dosage unit of claim 1, wherein the first preparation is a neutraceutical formulation.

3. The dosage unit of claim 1, wherein the first preparation is a herbal formulation.

4. The dosage unit of claim 1, wherein the first preparation is a nutritional supplement.

5. The dosage unit of claim 1, wherein the first preparation comprises a mixture of fennel and fenugreek.

6. The dosage unit of claim 1, wherein the paraprobiotics are obtained by inactivating said probiotics after culturing the probiotics in a growth medium containing milk or milk-derived ingredients.

* * * * *